(12) United States Patent
Beaucage et al.

(10) Patent No.: US 11,987,599 B2
(45) Date of Patent: May 21, 2024

(54) SOLID SUPPORT FOR SYNTHESIZING NUCLEIC ACID SEQUENCES AND METHODS FOR MAKING AND USING

(71) Applicant: United States of America, as represented by the Secretary, Department of Health and Human Services, Silver Spring, MD (US)

(72) Inventors: Serge L. Beaucage, Silver Spring, MD (US); Andrzej M. Grajkowski, Kensington, MD (US)

(73) Assignee: United States of America, as represented by the Secretary, Department of Health and Human Services, Silver Spring, MD (US)

( * ) Notice: Subject to any disclaimer, the term of this patent is extended or adjusted under 35 U.S.C. 154(b) by 0 days.

(21) Appl. No.: 18/003,404

(22) PCT Filed: Jun. 28, 2021

(86) PCT No.: PCT/US2021/039403
§ 371 (c)(1),
(2) Date: Dec. 27, 2022

(87) PCT Pub. No.: WO2022/005988
PCT Pub. Date: Jan. 6, 2022

(65) Prior Publication Data
US 2023/0271998 A1    Aug. 31, 2023

Related U.S. Application Data

(60) Provisional application No. 63/046,413, filed on Jun. 30, 2020.

(51) Int. Cl.
*C07H 21/04*       (2006.01)
*C07F 9/09*        (2006.01)
*C07F 9/655*       (2006.01)
*C07H 21/00*       (2006.01)
*C07H 21/02*       (2006.01)
*C12N 15/10*       (2006.01)
*C12N 15/113*      (2010.01)
*C40B 50/18*       (2006.01)

(52) U.S. Cl.
CPC .............. *C07H 21/04* (2013.01); *C07F 9/093* (2013.01); *C07F 9/098* (2013.01); *C07F 9/65515* (2013.01); *C07H 21/00* (2013.01); *C07H 21/02* (2013.01); *C12N 15/1068* (2013.01); *C12N 15/113* (2013.01); *C40B 50/18* (2013.01)

(58) Field of Classification Search
CPC ......... C07F 9/093; C07H 21/00; C07H 21/02; C07H 21/04
See application file for complete search history.

(56) References Cited

FOREIGN PATENT DOCUMENTS

WO    WO-2021173615 A1 * 9/2021 .............. C07F 9/098

OTHER PUBLICATIONS

Plutowski et al., "DNA-Based Self-Sorting of Nanoparticles on Gold Surfaces" Advanced Materials vol. 19 pp. 1951-1956 DOI: 10.1002/adma.200602169 (Year: 2007).*
Ellington et al., "Synthesis and Purification of Oligonucleotides" Current Protocols in Molecular Biology, Supplement 42, 2.11.1-2.11.25 (Year: 1998).*
Grajkowski et al., "The 2-(N-Formyl-N-methyl)aminoethyl Group as a Potential Phosphate/ Thiophosphate Protecting Group in Solid-Phase Oligodeoxyribonucleotide" Organic Letters vol. vol. 3 No. 9, pp. 1287-1290 (Year: 2001).*
Bonora et al., "HELP (High Efficiency Liquid Phase) new oligonucleotide synthesis on soluble polymeric support," *Nucleic Acid Research* 18(11): 3155-3159, 1990.
Chi et al., "Safety of antisense oligonucleotides and siRNA-based therapeutics," *Drug Discovery Today* 22(5):823-833, May 2017.
Crooke et al., "Integrated safety Assessment of 2'-O-Methoxyethyl Chimeric Antisense Oligonucleotides in NonHuman Primates and Healthy Human Volunteers," *Official Journal of the American Society of Gene & Cell Therapy* 24(10):1771-1782, Oct. 2016.
Gao et al., "H-Phosphate Oligonucleotide Synthesis On a Polyethylene Glycol/Polystyrene Copolymer," *Tetrahedron Letters* 32(4o):5477-5480, 1991.
Grajkowski et al., "Thermolytic Release of Covalently Linked DNA Oligonucleotides and Their Conjugates from Controlled-Pore Glass at Near Neutral pH," *Bioconjugate Chemistry* 19(8): 1696-1706, Jul. 23, 2008 (Abstract Only).
Grajkowski et al., "An expedient process for reducing the formation of process-related impurities during solid-phase synthesis of potential nucleic acid-based drugs," *Bioorganic & Medicinal Chemistry* 28(22):115779 (7 pages), Sep. 24, 2020.

(Continued)

*Primary Examiner* — Eric Olson
(74) *Attorney, Agent, or Firm* — Klarquist Sparkman, LLP

(57) ABSTRACT

Disclosed herein are embodiments of a solid support suitable for synthesizing nucleic acid sequences. The solid support may have a structure according to Formula I, where CPG is controlled pore glass, and m, n, x, y, $R^1$ and $R^2$ are as defined herein.

Formula I

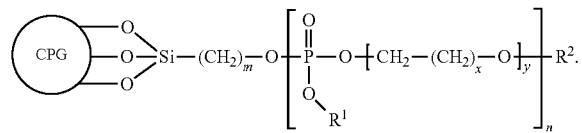

Also disclosed are methods for making and using the solid support, kits including solid support, and a universal linker phosphoramidite suitable for use in the solid support.

33 Claims, 9 Drawing Sheets
Specification includes a Sequence Listing.

(56) References Cited

OTHER PUBLICATIONS

Grajkowski et al., "An Improved PEG-Linked Solid Support for Minimizing Process-Related Impurities During Solid-Phase Synthesis of DNA and RNA Sequences," *Current Protocols* 1(5):e108, May 1, 2021 (Abstract Only).

International Search Report dated Dec. 20, 2021 from International Application No. PCT/US2021/039403 (8 pages).

Katzhendler et al., "Spacer Effect on the Synthesis of Oligodeoxynucleotides by the Phosphite method," *Reactive Polymers* 6:175-187, 1987.

Katzhendler et al., "The Effect of Spacer, Linkage and Solid Support on the Synthesis of Oligonucleotides," *Tetrahedron* 45(9):2777-2792, 1989.

Kwiatkowski et al., "Synthesis of full-length oligonucleotides: cleavage of apurinic molecules on a novel support," *Nucleic Acids Research* 24(23):4632-4640, 1996.

Temsamani et al., "Sequence identity of the n-1 product of a synthetic oligonucleotide," *Nucleic Acids Research* 23(11):1841-1844, 1995.

Written Opinion dated Dec. 20, 2021 from International Application No. PCT/US2021/039403 (13 pages).

\* cited by examiner

SEQUENCE LISTING

<160> NUMBER OF SEQ ID NOS: 5

<210> SEQ ID NO 1
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 1
ctgagtagcg aacgtgaaga                                           20

<210> SEQ ID NO 2
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 2
tcttggttac atgaaatcct                                           20

<210> SEQ ID NO 3
<211> LENGTH: 20
<212> TYPE: RNA
<213> ORGANISM: Artificial sequence
<220> FEATURE:
<223> OTHER INFORMATION: Synthetic nucleic acid

<400> SEQUENCE: 3
ucuugguuac augaaauccu                                           20

<210> SEQ ID NO 4
<211> LENGTH: 20
<212> TYPE: DNA
<213> ORGANISM: Artificial sequence

```
<220> FEATURE:
<223> OTHER INFORMATION: Synthetic nucleic acid

<400> SEQUENCE: 4
ctctgtacct tacgtcttcg                                              20

<210> SEQ ID NO 5
<211> LENGTH: 20
<212> TYPE: DNA
<213> ORGANISM: Artificial sequence
<220> FEATURE:
<223> OTHER INFORMATION: Sythetic nucleic acid

<400> SEQUENCE: 5
atagtgtgca tcgatgccac                                              20
```

SOLID SUPPORT FOR SYNTHESIZING NUCLEIC ACID SEQUENCES AND METHODS FOR MAKING AND USING

CROSS REFERENCE TO RELATED APPLICATIONS

This is the U.S. National Stage of International Application No. PCT/US2021/039403, filed Jun. 28, 2021, which was published in English under PCT Article 21(2), which in turn claims the benefit the earlier filing date of U.S. provisional patent application No. 63/046,413, filed Jun. 30, 2020, which applications are incorporated herein by reference in their entireties.

FIELD

The application concerns a solid support for synthesizing nucleic acid sequences and methods for making and using the solid support.

INCORPORATION OF ELECTRONIC SEQUENCE LISTING

The electronic sequence listing, submitted as a text file named Sequence listing.txt (4,096 bytes), created on Apr. 6, 2023, is herein incorporated by reference in its entirety.

BACKGROUND

The purity of synthetic nucleic acid sequences is important for the production of safe and efficacious nucleic acid-based drugs, such as those for antisense or RNA interference in vivo therapies. Highly pure synthetic DNA sequences are also important for the construction of entire genes to be used in synthetic biology applications (e.g., mRNA and/or genome editing). Although the use of antisense DNA (asDNA) sequences or small interfering RNA (siRNA) duplexes have been demonstrated to be highly potent at silencing the expression of disease-causing proteins in vitro, the clinical applications of these nucleic acid sequences for the treatment of human diseases has been hindered by various factors including: (i) instability in biological media; (ii) poor delivery to target cells; (iii) poor uptake by target cells and; (iv) dose-related toxicities. Severe thrombocytopenic or peripheral neuropathy adverse events have been reported in patients treated with asDNA sequences or siRNAs, respectively. These limitations have prompted the use of chemical modifications and/or formulations to improve nuclease resistance and binding affinity of asDNAs to their respective targets with the aims of enhancing cellular delivery, potency and efficacy of nucleic acid-based drugs. Identification of the root cause leading to adverse events associated with the use of asDNA sequences is challenging given the various structural modifications made to DNA sequences to ensure their stability in a biological environment and affinity to targeted mRNA sequences. Furthermore, even though the phosphoramidite-based manufacture of synthetic DNA and RNA sequences is highly efficient, synthetic DNA and RNA sequences are still contaminated with process-related impurities. These impurities include partially protected and/or 5'-uncapped DNA or RNA sequences leading to the production of shorter than full-length sequences. The distinct shorter than full-length (n−1) DNA sequences are difficult to remove from the full-length DNA product and can potentially elicit immune responses and/or adverse events arising from off-target activities upon administration to patients under antisense therapy settings. Accordingly, there is a need to minimize the formation of those process-related impurities to levels that should not become a safety concerns to patients.

SUMMARY

Disclosed herein are embodiments of a solid support suitable for solid phase synthesis of nucleic acid sequences. Using the disclosed solid support may result in a nucleic acid composition that has a reduced amount of impurities, compared to the same nucleic acid sequence being produced using current commercially available solid supports. In some embodiments, the disclosed solid support has a structure according to Formula I

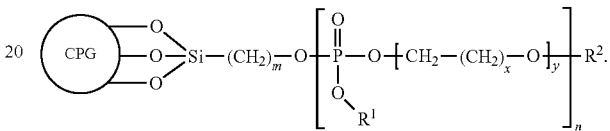

Formula I

With respect to Formula I, CPG is controlled pore glass. m is from 2 to 6, such as 2, 3, 4, 5, or 6, and in some embodiments, m is 2, 3 or 4, and may be 3. x is from 1 to 5, such as 1, 2, 3, 4, or 5, and in some embodiments, x is 1, 2 or 3, and may be 1. y is from 2 to 12, and in some embodiments, y is from 3 to 10, and may be 6. n is from 3 to 10, such as 3, 4, 5, 6, 7, 8, 9 or 10, and in some embodiments, n is from 3 to 7, and may be 5. And each $R^1$ independently $C_{1-6}$alkyl, $-(CH_2)_{1-6}CN$, $-(CH_2)_{1-6}OR'$ or a thermolabile phosphate protecting group, where R' is aliphatic, aryl, or aralkyl. $R^1$ may be $C_{1-4}$alkyl or $-(CH_2)_{1-4}CN$, and in certain embodiments, $R^1$ is $-CH_2CH_2CN$.

In any embodiments, $R^2$ may be H,

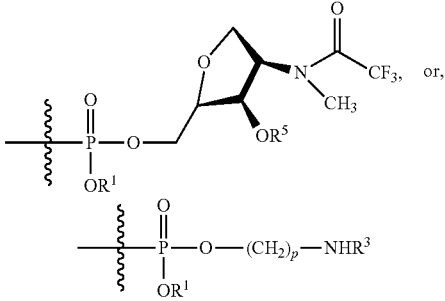

where p is from 2 to 10, such as 2, 3, 4, 5, 6, 7, 8, 9 or 10, and in certain embodiments, p is 6. And $R^3$ may be H or

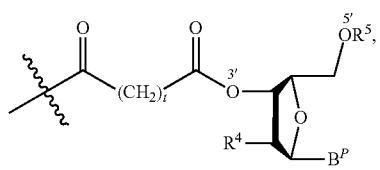

where t is 1, 2, 3 or 4, and may be 2; $R^4$ is H or $OR^6$; and $B^P$ is a nucleic acid base where the exocyclic amine group, if present, is protected.

$R^5$ is PG or a nucleic acid sequence, where PG is a protecting group. In any embodiments, PG may be 4,4'-dimethoxytrityl (DMTr).

$R^6$ may be 9-phenylxanthyl (pixyl), tert-butyldimethylsilyl (TBDMS), tert-butyldiphenylsilyl (TBDPS), trimethylsilyl (TMS), triethylsilyl (TES), triisopropylsilyl (TIPS), and in some embodiments, $R^6$ is TBDMS.

m, x, y and n may be selected to produce a support backbone length from the silicon atom to the $R^2$ moiety of from 50 atoms to 400 atoms, such as from 100 atoms to 150 atoms.

In any embodiments, $B^P$ may be a nucleic acid base with exocyclic amine group(s) protected if present, such as exocyclic amine-protected adenine, exocyclic amine-protected cytosine, exocyclic amine-protected guanine, thymine, uracil, hypoxanthine, xanthine, exocyclic amine-protected 7-methylguanine, 5,6-dihydrouracil, exocyclic amine-protected 5-methylcytosine, or exocyclic amine-protected 5-hydroxymethylcytosine, and may be exocyclic amine-protected adenine, exocyclic amine-protected cytosine, exocyclic amine-protected guanine, thymine, or uracil. In some embodiments, $B^P$ is adenine, cytosine, or guanine, where the exocyclic amine is protected by a benzoyl (Bz), isobutyryl (iBu), phenoxyacetyl (Pac), phenyl sulfonylethoxycarbonyl, p-nitrophenyloxycarbonyl, allyloxycarbonyl, or levulinyl group. In other embodiments, $B^P$ is thymine or uracil.

In some embodiments, $R^4$ is H and/or $B^P$ is exocyclic amine-protected adenine, exocyclic amine-protected cytosine, exocyclic amine-protected guanine, or thymine. In other embodiments, $R^4$ is $OR^6$ and/or $B^P$ is exocyclic amine-protected adenine, exocyclic amine-protected cytosine, exocyclic amine-protected guanine, or uracil. In such embodiments, $R^6$ may be TBDMS, TBDPS, TMS, TES, or TIPS, such as TBDMS.

Exocyclic amine-protected adenine may be $N^6$-benzoyl adenine ($A^{Bz}$) or $N^6$-phenoxyacetyl adenine ($A^{Pac}$). Exocyclic amine-protected cytosine may be $N^4$-benzoyl cytosine ($C^{Bz}$) or $N^4$-phenoxyacetyl cytosine ($C^{Pac}$). And/or Exocyclic amine-protected guanine may be $N^2$-isobutyryl guanine ($G^{iBu}$) or $N^2$-phenoxyacetyl guanine ($G^{Pac}$).

In any embodiments, a loading of the support on the CPG may be from 5 μmol/g to about 125 μmol/g.

And in some embodiments, the solid support has a formula selected from:

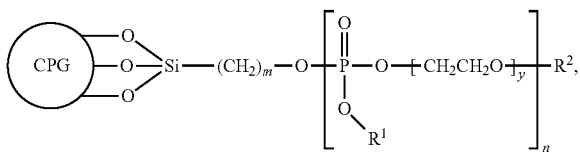

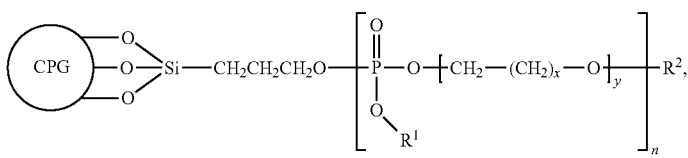

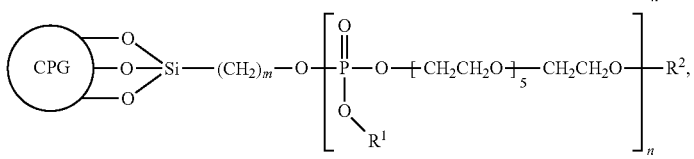

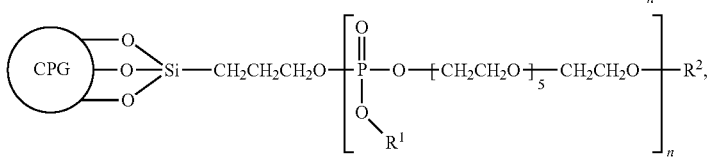

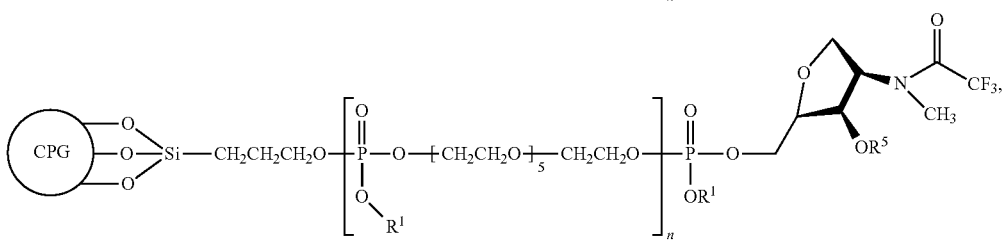

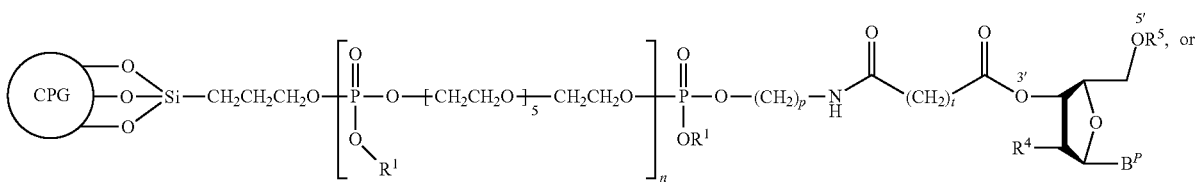

-continued

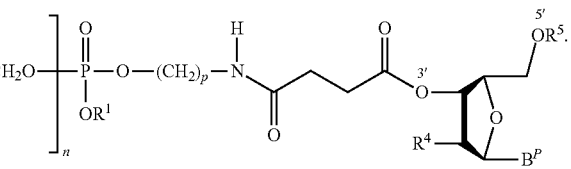

In any embodiments, t may be 2. Also in any embodiments, $R^5$ may be PG, and in some embodiments, is DMTr. Alternatively, $R^5$ may be a nucleic acid sequence, and may comprise one or more DNA sequences, such as one or more antisense DNA sequences. In other embodiments, the nucleic acid sequence comprises one or more RNA sequences, such as one or more antisense RNA sequences, one or more microRNA (miRNA) sequences, one or more small interfering RNA (siRNA) sequences, one or more repeat-associated small interfering RNA (rasiRNA) sequences, or combinations thereof.

Also disclosed is a universal linker phosphoramidite suitable for use with certain embodiments of the disclosed solid support. The universal linker may have a structure:

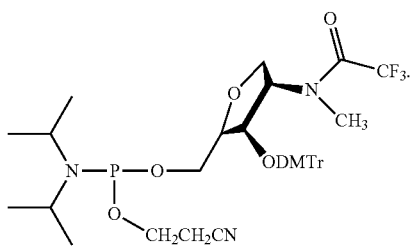

Embodiments of a method for synthesizing a nucleic acid sequence using the disclosed solid support also are disclosed herein. In some embodiments, the method comprises loading a solid support according to any one of the disclosed embodiments into a DNA/RNA synthesizer, and operating the synthesizer to produce a desired nucleic acid sequence. In some embodiments, the solid support is a solid support where $R^5$ is PG, such as DMTr.

Also disclosed herein is a kit comprising a solid support according to any one of the disclosed embodiments, and may comprise a protected 2'-deoxynucleoside, ribonucleoside, and/or chemically modified nucleoside wherein an exocyclic amine on the deoxynucleoside, ribonucleoside or chemically modified nucleoside, if present, also is protected. The 2'-deoxynucleoside may be DMTrdA$^{Bz}$, DMTrdC$^{Bz}$, DMTrdG$^{iBu}$, or DMTrT), and/or the ribonucleosides may be DMTrA$^{Pac}$-2'-OTBDMS, DMTrC$^{Pac}$-2'-OTBDMS, DMTrG$^{Pac}$-2'-OTBDMS, or DMTrU-2'-OTBDMS. In some embodiments, the kit comprises a universal linker phosphoramidite, such as the universal linker phosphoramidite disclosed herein. In some embodiments, the kit further comprises ammonium hydroxide.

The foregoing and other objects and features of the disclosure will become more apparent from the following detailed description, which proceeds with reference to the accompanying figures.

SEQUENCE LISTING

Figure 1:
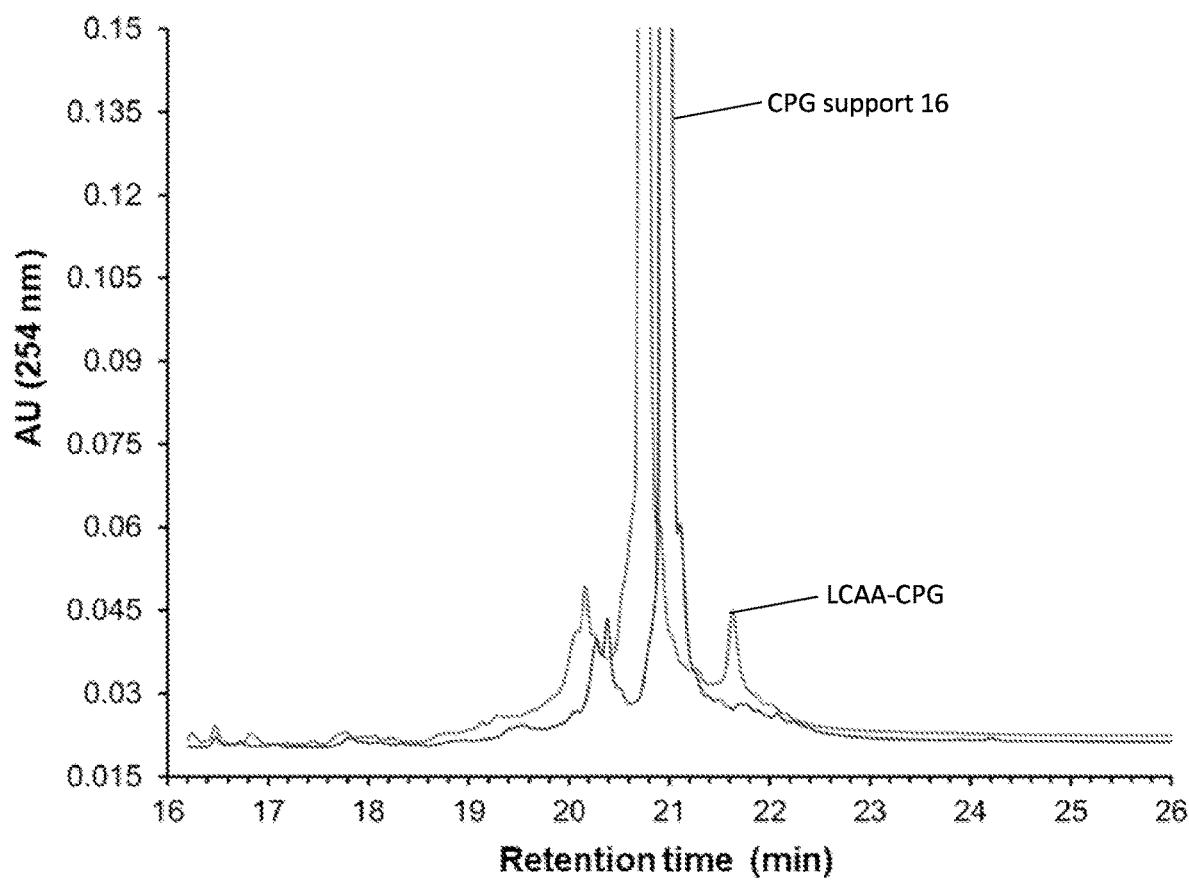
FIG. 1 is a graph of retention time versus absorbance units at 254 nm, illustrating the HPLC profiles of unpurified 5'-d(CTGAGTAGCGAACGTGAAGA) (SEQ ID NO: 1) produced by an embodiment of the disclosed solid support structure comprising 3 hexaethylene glycol phosphate repeating units, and comparing it to the same sequence produced using a commercial long chain alkylamine-controlled pore glass (LCAA-CPG) support.

The nucleic acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. The Sequence Listing is submitted as an ASCII text file, created on Jun. 28, 2021, 4 KB, which is incorporated by reference herein in its entirety. In the accompanying sequence listing:

SEQ ID NOs: 1-5 are nucleic acid sequences produced using exemplary embodiments of the disclosed solid support structure.

DETAILED DESCRIPTION

I. Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entireties.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include implicit hydrogens such that each carbon conforms to a valence of four. For example, in the structure on the left-hand side of the schematic below there are nine hydrogen atoms implied. The nine hydrogen atoms are depicted in the right-hand structure

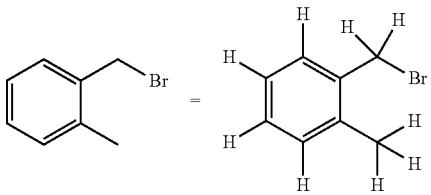

Sometimes a particular atom in a structure is described in textual formula as having a hydrogen or hydrogen atoms, for example —$CH_2CH_2$—. It will be understood by a person of ordinary skill in the art that the aforementioned descriptive techniques are common in the chemical arts to provide brevity and simplicity to description of organic structures.

A person of ordinary skill in the art will appreciate that compounds, such as the solid supports disclosed herein, may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diastereomers, and mixtures thereof, such as racemic mixtures. In certain embodiments the compounds disclosed herein are synthesized in or are purified to be in substantially enantiopure form, such as in an 85% enantiomeric excess (e.e.), a 90% enantiomeric excess, a 95% enantiomeric excess, a 97% enantiomeric excess, a 98% enantiomeric excess, a 99% enantiomeric excess, or even in greater than a 99% enantiomeric excess, such as in a substantially enantiopure form. In other embodiments, the compounds are in a racemic form, having substantially a 50:50 mixture of enantiomers.

As another example, certain disclosed compounds can exist in several tautomeric forms, including the enol form, the keto form, and mixtures thereof. For example, a compound may have a moiety exhibiting the following isomerization:

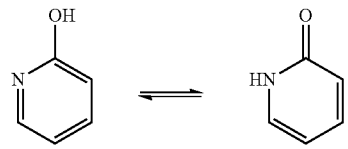 [SMILES: Oc1ccccn1 ; O=c1cccc[nH]1]

As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. In cases of limited rotation, e.g. around the amide bond, atropisomers are also possible and are also specifically included in the compounds of the invention.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium, such as in $C_2D_xH_{5-x}$.

As used herein, the term "substituted" refers to all subsequent modifiers in a term, for example in the term "substituted aryl$C_{1-8}$alkyl," substitution may occur on the "$C_{1-8}$ alkyl" portion, the "aryl" portion or both portions of the aryl$C_{1-8}$alkyl group.

Aliphatic: A substantially hydrocarbon-based group or moiety. An aliphatic group or moiety can be acyclic, including alkyl, alkenyl, or alkynyl groups, cyclic versions thereof, such as cycloaliphatic and/or spiroaliphatic groups or moieties including cycloalkyl, cycloalkenyl, cycloalkynyl, or spiroalkyl and further including straight- and branched-chain arrangements, and all stereo and position isomers as well. Unless expressly stated otherwise, an aliphatic group contains from one to twenty-five carbon atoms ($C_{1-25}$), for example, from one to fifteen ($C_{1-15}$), from one to ten ($C_{1-10}$) from one to six ($C_{1-6}$), or from one to four carbon atoms ($C_{1-4}$) for an acyclic alkyl group or moiety; from two to twenty-five carbon atoms ($C_{1-25}$) for example, from two to fifteen ($C_{1-15}$), from two to ten ($C_{1-10}$) from two to six ($C_{1-6}$), or from two to four carbon atoms ($C_{1-4}$) for an acyclic alkenyl or alkynyl group or moiety; from three to fifteen carbon atoms ($C_{3-15}$), such as from three to ten ($C_{3-10}$), from three to eight ($C_{3-8}$), from three to six ($C_{3-6}$), or from three to four ($C_{3-4}$) carbon atoms for a cycloaliphatic group or moiety; or from three to fifteen ($C_{6-15}$) carbon atoms for a spiroaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group).

Alkyl: A saturated aliphatic hydrocarbyl group having from 1 to 10 ($C_{1-10}$) or more carbon atoms, more typically 1 to 8 ($C_{1-8}$) carbon atoms such as 1 to 6 ($C_{1-6}$) carbon atoms or 1 to 4 ($C_{1-4}$) carbon atoms. An alkyl moiety may be substituted or unsubstituted. This term includes, by way of example, linear and branched hydrocarbyl groups such as methyl ($CH_3$), ethyl (—$CH_2CH_3$), n-propyl (—$CH_2CH_2CH_3$), isopropyl (—$CH(CH_3)_2$), n-butyl (—$CH_2$—$CH_2CH_2CH_3$), or isobutyl (—$CH_2CH_2(CH_3)_2$).

Cycloaliphatic: Refers to a cyclic aliphatic group having a single ring (e.g., cyclohexyl), or multiple rings, such as in a fused, bridged or spirocyclic system, at least one of which is aliphatic. Typically, the point of attachment to the parent structure is through an aliphatic portion of the multiple ring system. Cycloaliphatic includes saturated and unsaturated systems, including cycloalkyl, cycloalkenyl and cycloalkynyl. A cycloaliphatic group may contain from three to twenty-five carbon atoms; for example, from three to fifteen, from three to ten, or from three to six carbon atoms. Unless otherwise stated, a cycloaliphatic group may be substituted or unsubstituted. Exemplary cycloaliphatic groups include, but are not limited to, cyclopropyl, cyclobutyl, cyclopentyl, cyclohexyl, cycloheptyl, cyclopentenyl, or cyclohexenyl.

Aryl: Refers to an aromatic carbocyclic group of, unless specified otherwise, from 6 to 15 carbon atoms having a single ring (e.g., phenyl) or multiple condensed rings in which at least one ring is aromatic (e.g., naphthalene). If any aromatic ring portion contains a heteroatom, the group is heteroaryl and not aryl. Aryl groups may be, for example, monocyclic, bicyclic, tricyclic or tetracyclic. Unless otherwise stated, an aryl group may be substituted or unsubstituted.

Aralkyl: Refers to an aryl group attached to the parent via an alkyl moiety. Exemplary aralkyl groups include benzyl and phenylethyl.

Exocyclic amine: As used herein, an exocyclic amine is an amine moiety that is not part of a ring structure, i.e., the nitrogen atom of the exocyclic amine is not a ring atom. Exemplary exocyclic amines include, but are not limited to, the amine at the $N^6$ position of adenine, the amine at the $N^2$ position of guanine, and the amine at the $N^4$ position of cytosine. An exocyclic amine may be unprotected or protected, such as by a suitable amine protecting group. Exemplary protecting groups include, but are not limited to, isobutyryl(iBu); phenoxyacetyl (Pac); levulinyl; amidine protecting groups, such as

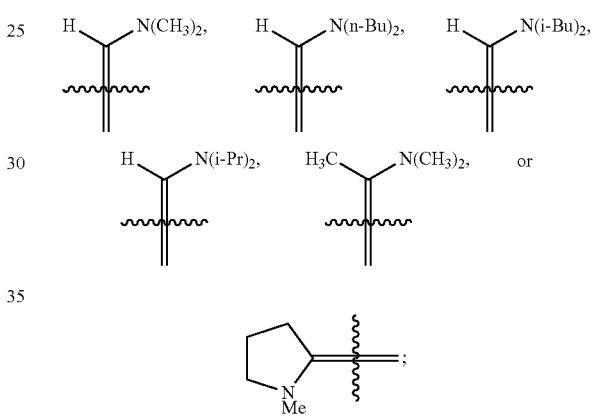

carbamate protecting groups, such as 9-fluorenylmethyl carbamate (Fmoc), 1,1-dimethyl-2,2,2-trichloroethyl carbamate (TCBOC),

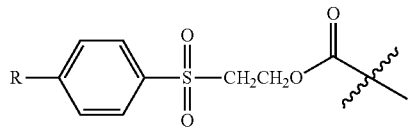

(where R is H, Cl or $NO_2$), 2-(4-nitrophenyl)ethyl carbamate, benzyl carbamate (Cbz), allyl carbamate (allyloxycarbonyl), 4-nitrophenyloxycarbonyl, or $(CH_3)_2CHCH_2OC$ (=O)—; or amide protecting groups, such as formamide, acetamide, $CH_3CH_3C(=O)—$, $(CH_3)_2CHC(=O)—$, $(CH_3)_3 CC(=O)—$,

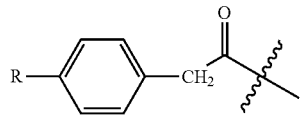

(where R is H or CMe₃), (Ph)₂CHC(=O)—,

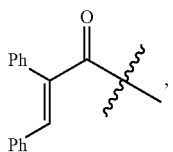

MeOCH₂C(=O)—, i-PrOCH₂C(=O)—,

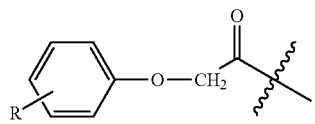

(where R is H, 2-Cl or 4-t-butyl), MeC(=O)CH₂CH₂C(=O)—, benzoyl (Bz),

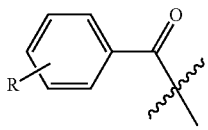

(where R is 4-methoxy, 4-Cl, 4-nitro, 4-NMe₂, 4-tert-butyl, 2-methyl, 3-Cl, 3,4-dichloro, or 3-methoxy-4-phenoxy),

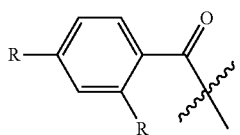

(where R is Me or MeO),

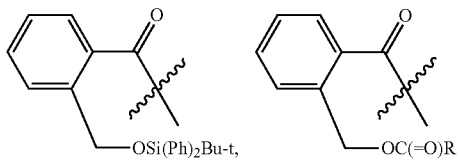

(where R is Ac, or Ph), PhN=NPh-C(=O)—,

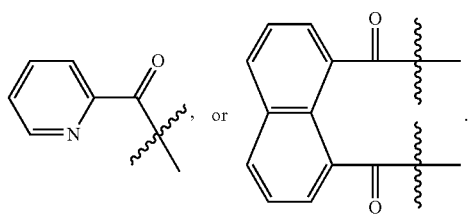 [SMILES: *C(=O)c1ccccn1 ; *C(=O)c1cccc2cccc(C(*)=O)c12]

Additional information concerning protecting groups for exocyclic amines on nucleic acid bases can be found in Beaucage, S. L. and Iyer, R. L. "Advances in the Synthesis of Oligonucleotides by the Phosphoramidite Approach," Tetrahedron, 1992, Vol. 48(12), pp 2223-2311, which is incorporated herein by reference in its entirety.

Heteroaryl: An aromatic group or moiety of, unless specified otherwise, from 5 to 15 ring atoms comprising at least one carbon atom and at least one heteroatom, such as N, S, O, P, or Si, preferably N, S or O. A heteroaryl group or moiety may comprise a single ring (e.g., pyridinyl, or pyrazine) or multiple condensed rings (e.g., indolyl). Heteroaryl groups or moiety may be, for example, monocyclic, bicyclic, tricyclic or tetracyclic. Unless otherwise stated, a heteroaryl group or moiety may be substituted or unsubstituted.

Heterocyclyl, heterocyclo or heterocycle: Aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, phosphorus, oxygen, silicon or sulfur atom(s), preferably N, S or O. The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and any nitrogen, phosphorus, carbon, silicon or sulfur atoms in the heterocyclyl moiety can be optionally oxidized to various oxidation states. For convenience, nitrogens, particularly, but not exclusively, those defined as annular aromatic nitrogens, are meant to include their corresponding N-oxide form, although not explicitly defined as such in a particular example. Thus, for a compound having, for example, a pyridinyl ring, the corresponding pyridinyl-N-oxide is included as another compound of the invention, unless expressly excluded or excluded by context. In addition, annular nitrogen atoms can be optionally quaternized. Heterocycle includes heteroaryl moieties, and heterocycloaliphatic moieties, such as heterocycloalkyl moieties, which are heterocyclyl rings that are partially or fully saturated. Unless otherwise stated, a heterocyclyl group or moiety may be substituted or unsubstituted. Examples of heterocyclyl groups include, but are not limited to, azetidinyl, oxetanyl, acridinyl, benzodioxolyl, benzodioxanyl, benzofuranyl, dioxolanyl, indolizinyl, naphthyridinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, and oxadiazolyl.

Halo, halide or halogen: Refers to fluoro, chloro, bromo or iodo.

Nucleic acid sequence: Refers to DNA and RNA sequences, such as cDNA and mRNA. In one examples, includes antisense nucleic acid sequences (such as antisense RNA or antisense DNA), microRNAs (miRNAs), small interfering RNAs (siRNAs), and repeat-associated small interfering RNAs (rasiRNAs). In one example, a nucleic acid sequence is a therapeutic nucleic acid sequence, such as a DNA therapeutic (e.g., antisense oligonucleotide, DNA aptamers) or RNA therapeutic (e.g., miRNA, siRNA, ribozyme, or RNA decoy). A nucleic acid sequence can include naturally occurring and/or non-naturally occurring nucleotides.

Nucleosides: The major nucleosides of DNA are deoxyadenosine (dA), deoxyguanosine (dG), deoxycytidine (dC) and deoxythymidine (T). The major nucleosides of RNA are adenosine (rA), guanosine (rG), cytidine (rC) and uridine (U). Includes nucleosides containing modified bases and modified sugar moieties, for example as described in U.S. Pat. No. 5,866,336 to Nazarenko et al. (herein incorporated by reference). Examples of modified sugar moieties which may be used to modify nucleotides at any position on its structure include, but are not limited to: arabinose, 2-fluoroarabinose, xylose, and hexose. In one example, a nucleoside is a 2'-deoxynucleoside (dA, dC, dG, or T). In one example, a nucleoside is chemically modified (e.g., LNA, BNA or UNA).

II. Solid Support Structure

Disclosed herein is a solid support structure suitable for synthesizing nucleic acid sequences. Embodiments of the solid support structure may facilitate synthesizing nucleic acid sequences having reduced process-related impurities and/or increased yield, compared to the same sequence synthesized using commercial solid supports. The impurities may comprise, but are not limited to, nucleic acid sequences having shorter lengths than a desired nucleic acid sequence, such as one or more nucleotides shorter; partially alkylated thymine or uracil bases in DNA or RNA sequences, possibly resulting from exposure to acrylonitrile produced during the deprotection of 2-cyanoethyl phosphate protecting groups under basic conditions; and/or impurities from removed protecting groups, such as tert-butyldimethylsilyl fluoride or tetrabutylammonium fluoride, that may contaminate the sequence, particularly solid-phase purified RNA sequences.

In some embodiments, the disclosed solid support structure has a formula I:

Formula I

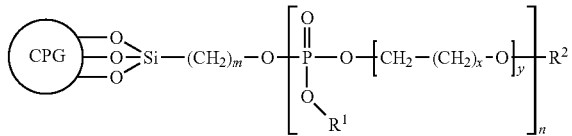

With respect to formula I, CPG is controlled pore glass. In some embodiments, the CPG has a pore size of from 250 Å to 1500 Å or more, such as from 500 Å to 1500 Å, from 500 Å to 1250 Å or from 500 Å to 1000 Å, and in certain embodiments, the CPG has a pore size of about 500 Å.

m is 2, 3, 4, 5, 6, such as 2, 3, or 4, and in certain embodiments, m is 3.

x is 1, 2, 3, 4, or 5, such as 1, 2, or 3. In some embodiments, x is 1 or 2, and in certain embodiments, x is 1.

y is from 2 to 12, such as 2, 3, 4, 5, 6, 7, 8, 9, 10, 11 or 12, and may be from 3 to 10, or from 4 to 8, and in some embodiments, y is 6.

n is from 3 to 10 or more, such as 3, 4, 5, 6, or 7, and may be 5, 6 or 7. In certain embodiments, n is 5.

In some embodiments, m, x, y and/or n are selected to produce a carbon/oxygen/phosphorus backbone chain from the silicon atom to the $R^2$ moiety of 50 atoms or more in length, such as from 50 atoms to 400 atoms, from 60 atoms to 350 atoms, from 100 atoms to 210 atoms, or from 100 atoms to 150 atoms.

Each $R^1$ independently is $C_{1-6}$alkyl, $-(CH_2)_{1-6}CN$, $-(CH_2)_{1-6}OR'$ or a thermolabile phosphate protecting group, where R' is aliphatic, aryl or aralkyl. R' may be alkyl, such as $C_{1-6}$alkyl; alkenyl, such as $C_{2-6}$alkenyl; alkynyl, such as $C_{2-6}$alkynyl; cycloalkyl, such as $C_{3-8}$cycloalkyl; aryl, such as phenyl; or aralkyl, such as benzyl. The thermolabile phosphate protecting group may have a structure

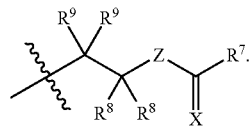

With respect to this structure, X is O or S.

$R^7$ is H, $R^a$, $OR^a$, $SR^a$, or $N(R^b)_2$, where $R^a$ is $R^d$; and $R^b$ is H, $R^d$ or two $R^b$s together with the nitrogen to which they are attached, form a 3- to 7-membered heterocyclyl.

Z is O, S, $N(R^c)$, $C(R^c)_2$ or $C(R^c)_2C(R^c)_2$ where each $R^c$ independently is H or $R^d$ or one $R^d$ in combination with the C=X moiety and one $R^a$ or $R^b$ from $R^7$ together form a 3- to 7-membered cycloaliphatic or heterocyclyl ring.

Each $R^8$ independently is H or $R^d$, or one $R^8$ together with Z forms an aryl ring, such as phenyl.

Each $R^9$ independently is H or $R^d$ or one $R^9$ and one $R^8$ together with the atoms to which they are attached, forms a moiety having a formula

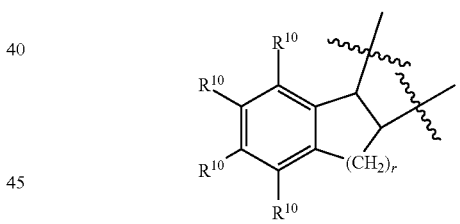

where r is 0 to 6, and each $R^{10}$ independently is H, $C_{1-6}$alkyl, $NO_2$, $-N(C_{1-6}alkyl)_2$, $-OC_{1-6}$alkyl, $-SC_{1-6}$alkyl, $-CN$, or halogen, provided that the aromatic ring substituted with $R^{10}$ is one carbon removed from the phosphate oxygen of Formula I.

$R^d$ is alkyl, alkenyl, alkynyl, cycloalkyl, aryl, or aralkyl.

In some embodiments, the thermolabile phosphate protecting group is selected from

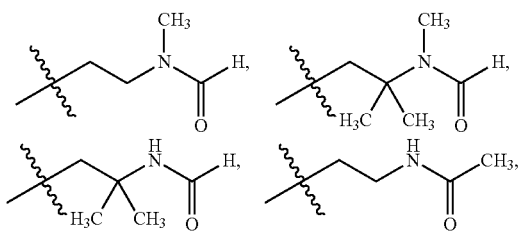

15

-continued

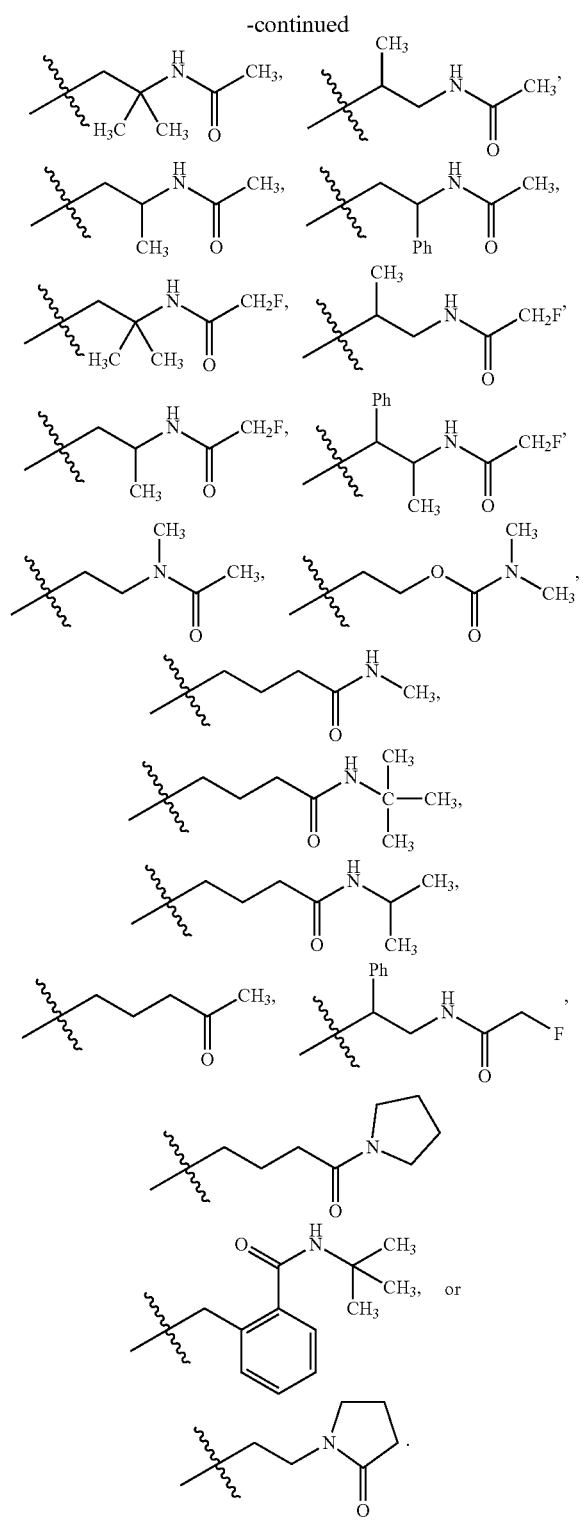

Additional information concerning thermolabile phosphate protecting groups can be found in U.S. Pat. No. 6,762,298, which is incorporated herein by reference in its entirety.

In some embodiments, each $R^1$ independently is $C_{1-4}$alkyl or $—(CH_2)_{1-4}CN$, and may be methyl, ethyl, propyl, $—CH_2CN$ or $—CH_2CH_2CN$, and in certain embodiments, $R^1$ is $—CH_2CH_2CN$.

In other embodiments, each $R^1$ independently is a thermolabile phosphate protecting group as defined herein.

16

And in some embodiments, each $R^1$ is the same, but in other embodiments, the support comprises two or more $R^1$ moieties, such as from 2 to the maximum number of $R^1$ moieties present in the structure. In certain embodiments, each $R^1$ is $—CH_2CH_2CN$.

$R^2$ is H,

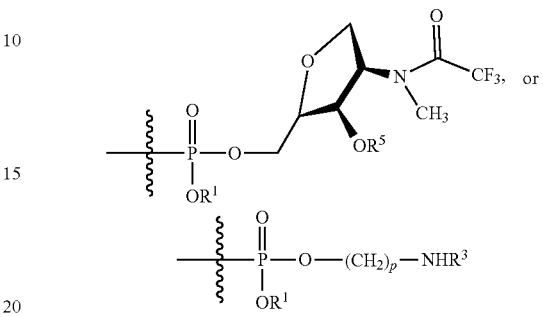

where p is from 2 to 10, such as from 3 to 8 or from 4 to 8, and in certain embodiments, p is 6.

$R^3$ is H or

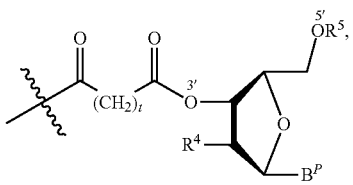

where t is 1, 2, 3 or 4, such as 2; $R^4$ is H or $OR^6$; and $B^P$ is a nucleic acid base where the exocyclic amine, if present, is protected. The protecting group can be any suitable protecting group, and may be a protecting group as disclosed herein. In some embodiments, $B^P$ is a nucleic acid where the exocyclic amine, if present, is protected by a benzoyl (Bz), isobutyryl(iBu), phenoxyacetyl (Pac), phenylsulfonylethoxycarbonyl, p-nitrophenyloxycarbonyl, allyloxycarbonyl, or levulinyl group. In certain embodiments, $B^P$ is $N^6$-benzoyl adenine ($A^{Bz}$), $N^4$-benzoyl cytosine ($C^{Bz}$), $N^2$-isobutyryl guanine ($G^{iBu}$), thymine (T), $N^6$-phenoxyacetyl adenine ($A^{Pac}$), $N^4$-phenoxyacetyl cytosine ($C^{Pac}$), $N^2$-phenoxyacetyl guanine ($G^{Pac}$), uracil (U), and/or similarly exocyclic amine-protected (where applicable) hypoxanthine, xanthine, 7-methylguanine, 5,6-dihydrouracil, 5-methylcytosine, or 5-hydroxymethylcytosine. Additional information concerning modified nucleic acid bases that can be used with the disclosed technology can be found in U.S. Pat. Nos. 7,355,037 and 7,612,197, which are incorporated herein by reference in their entireties. In some embodiments, $B^P$ is $A^{Bz}$, $C^{Bz}$, $G^{iBu}$, T or $A^{Pac}$, $C^{Pac}$, $G^{Pac}$, or U.

$R^5$ is PG or a nucleic acid sequence. The nucleic acid sequence may comprise one or more DNA sequences and/or one or more RNA sequences. An exemplary DNA sequence is an antisense DNA sequence. An exemplary RNA sequence is an antisense RNA sequence, microRNA (miRNA) sequence, small interfering RNA (siRNA) sequence, repeat-associated small interfering RNA (rasiRNA) sequence, or a combination thereof. A person of ordinary skill in the art understands that when $R^5$ is a nucleic acid sequence, the nucleic acid sequence is attached to the support via a phosphate moiety at the 3' end of the nucleic acid sequence, in the same manner as nucleotides are typically attached together to form a nucleic acid sequence.

$R^6$ is a hydroxyl protecting group that can be removed with fluoride ions or under essentially neutral conditions. Typically, $R^6$ is 9-phenylxanthyl (pixyl) or a silyl protecting group, such as tert-butyldimethylsilyl (TBDMS), tert-butyldiphenylsilyl (TBDPS), trimethylsilyl (TMS), triethylsilyl (TES), triisopropylsilyl (TIPS). In certain embodiments, $R^6$ is TBDMS, TBDPS, TMS, TES, TIPS, and may be TBDMS.

PG is any protecting group suitable for use in DNA or RNA synthesis. In some embodiments PG is dimethoxytrityl (DMTr), triphenylmethyl (trityl), p-monomethoxytrityl (MMTr), trimethoxytrityl (TMTr), 9-phenylxanthen-9-yl, 9-(p-methoxyphenyl)xanthen-9-yl, 9-phenylthioxanthen-9-yl, or 7-chloro-9-phenylthioxanthen-9-yl. In certain embodiments, PG is DMTr.

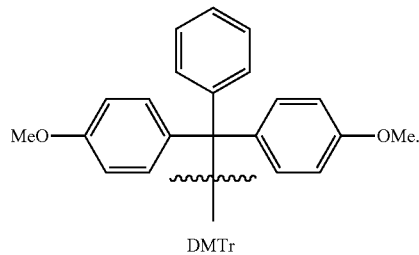 [SMILES: *C(c1ccccc1)(c1ccc(OC)cc1)c1ccc(OC)cc1]

DMTr

In some embodiments, $R^4$ is H and $B^P$ is an exocyclic amine-protected adenine, an exocyclic amine-protected cytosine, an exocyclic amine-protected guanine, or thymine, for example:

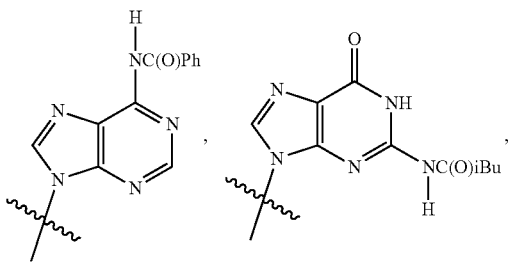

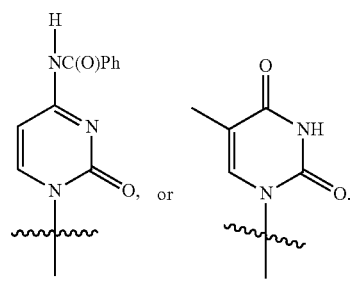

In other embodiments, $R^4$ is $OR^6$ and $B^P$ is an exocyclic amine-protected adenine, an exocyclic amine-protected cytosine, an exocyclic amine-protected guanine, or uracil, for example:

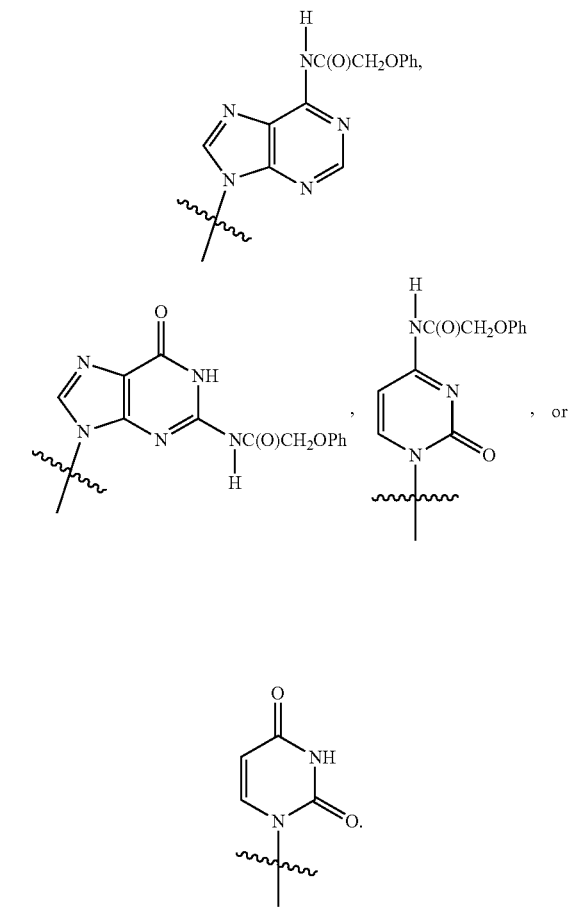

In some embodiments, x is 1, leading to a support structure according to Formula II:

Formula II

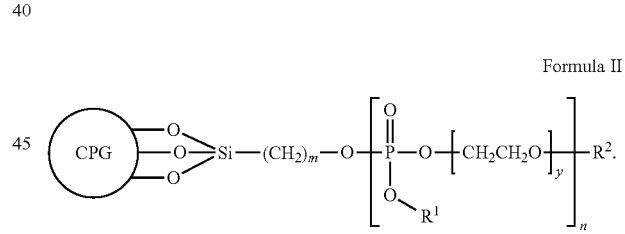

With respect to formula II, CPG, m, y, n, $R^1$ and $R^2$ are as previously defined for Formula I.

In some embodiments of Formulas I and II, y is 6. In particular embodiments, the solid support structure has a formula according to Formula III:

Formula III

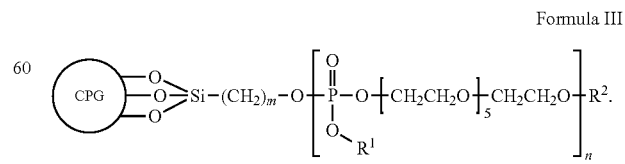

With respect to Formula III, CPG, m, n, $R^1$ and $R^2$ are as previously defined for Formula I.

In some embodiments of Formula I, m is 3, leading to solid support structure according to Formula IV

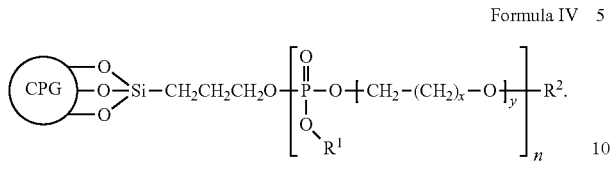

Formula IV

With respect to Formula IV, CPG, n, x, y, $R^1$ and $R^2$ are as previously defined for Formula I. In certain embodiments, of Formula IV, x is 1 and y is 6, leading to a solid support structure according to Formula V

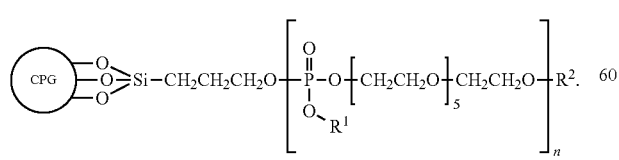

Formula V

With respect to Formula V, CPG, n, $R^1$ and $R^2$ are as previously defined for Formula I.

In some embodiments of Formulas I-V, $R^2$ is H.
In other embodiments of Formulas I to V, $R^2$ is

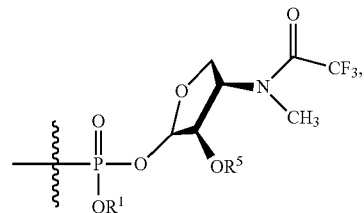

where $R^1$ and $R^5$ are as previously defined for Formula I. In certain embodiments, the solid support structure has a formula according to Formula VI or VII

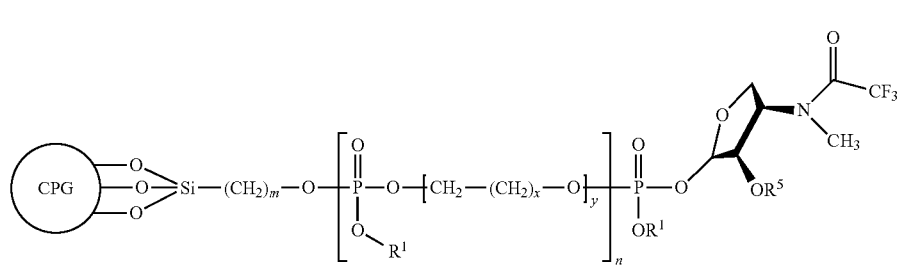

Formula VI

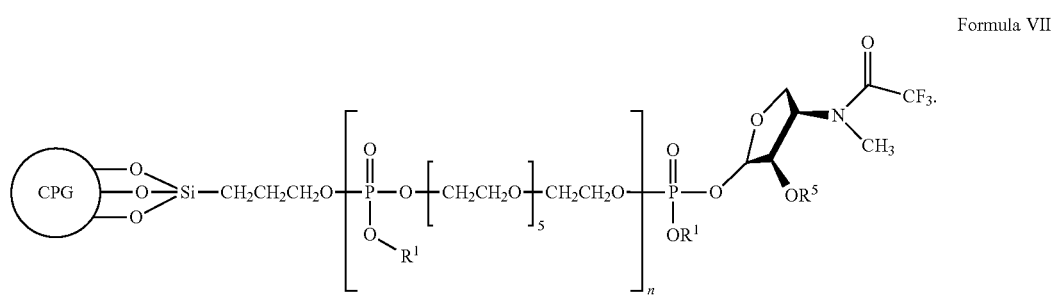

Formula VII

With respect to Formulas VI and VII, CPG, m, n, x, y, $R^1$ and $R^5$ are as previously defined for Formula I. In certain embodiments, of Formulas VI and VII, $R^5$ is PG, where PG is as previously defined for Formula I.

In some other embodiments of Formulas I to V, $R^2$ is

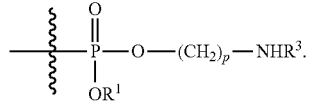

In certain embodiments, the solid support structure has a formula according to Formula VIII or IX

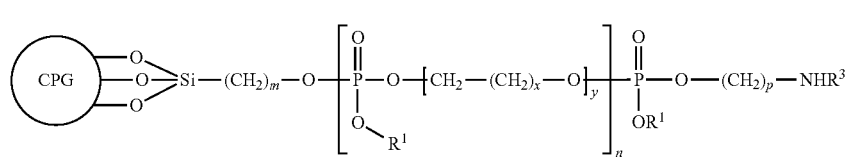

Formula VIII

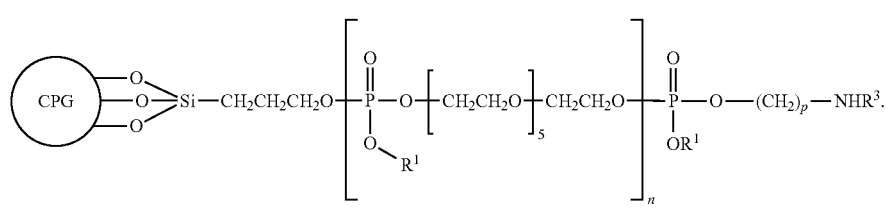

Formula IX

With respect to Formulas VIII and IX, CPG, m, n, p, x, y, $R^1$ and $R^3$ are as previously defined for Formula I.

In some embodiments of Formulas I-V or VIII-IX, $R^3$ is H. In other embodiments, $R^3$ is

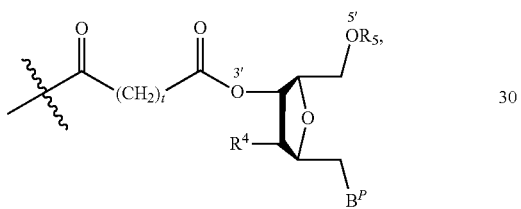

where t, $R^4$, $R^5$ and $B^P$ are as previously defined for Formula I. And in certain embodiments, the solid support structure has a formula according to Formula X, XI, XII or XIII

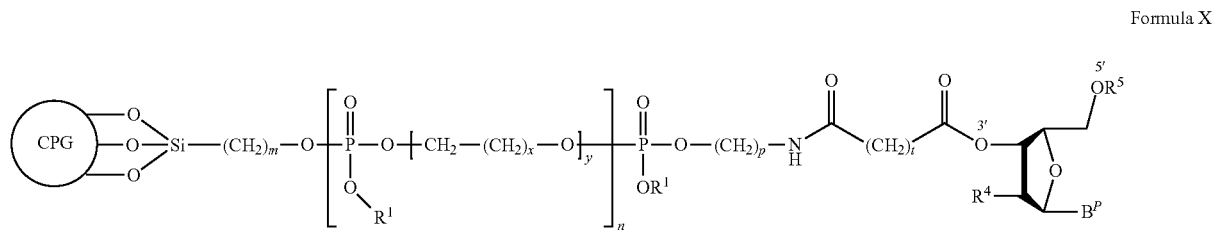

Formula X

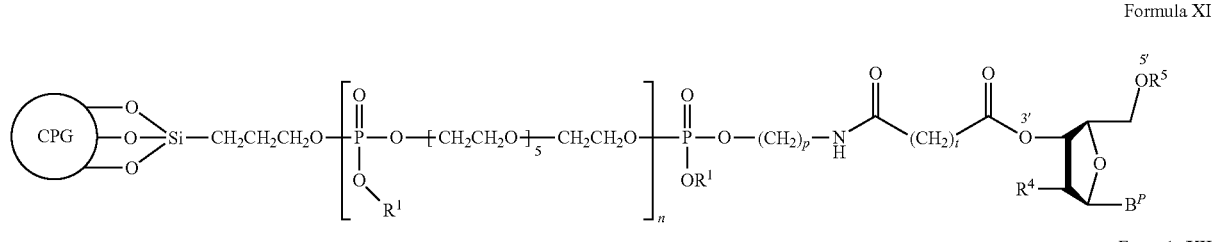

Formula XI

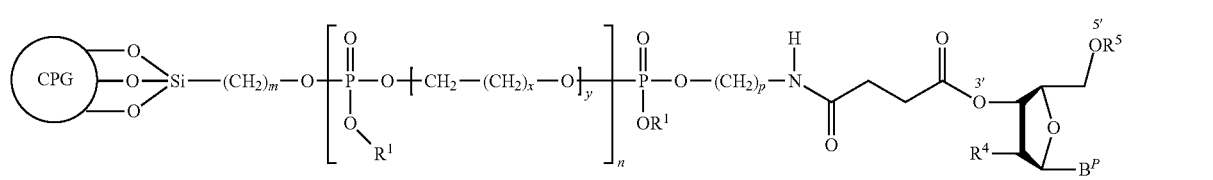

Formula XII

Formula XIII

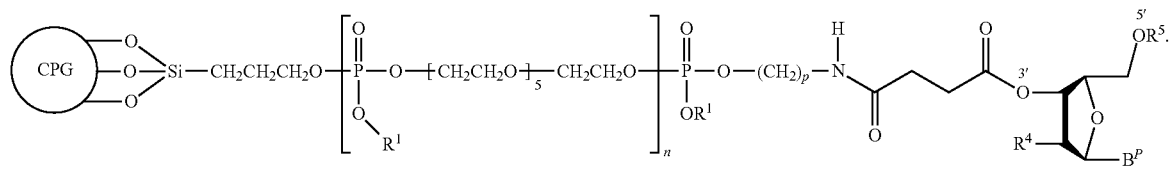

With respect to Formulas X-XIII, CPG, m, n, p, t, x, y, $R^1$, $R^4$, $R^5$, and $B^P$ are as previously defined for Formula I. In some embodiments, $R^5$ is PG.

In some embodiments of Formulas X-XIII, $R^4$ is H and $B^P$ is an exocyclic amine-protected adenine, an exocyclic amine-protected cytosine, an exocyclic amine-protected guanine, or thymine. In other embodiments of Formulas X-XIII, $R^4$ is $OR^6$ and $B^P$ is an exocyclic amine-protected adenine, an exocyclic amine-protected cytosine, an exocyclic amine-protected guanine, or uracil.

In particular embodiments of Formulas I-V and p is 6.

In any embodiments, each $R^1$ may be the same, and in certain embodiments, each $R^1$ is —$CH_2CH_2CN$.

In any embodiments, n is 3, 4, 5, 6, 7, 8, 9 or 10, such as 3, 4, 5, 6, or 7, and may be selected from 3, 5, or 7, or from 4, 5, 6 or 7, such as 5, 6, or 7. And in certain examples, n is 5.

In certain embodiments of Formulas I-XIII, $R^5$ is PG, such as DMTr. In other embodiments, $R^5$ is a nucleic acid sequence. In certain embodiments, $R^5$ is, or comprises, a DNA sequence. In certain other embodiments, $R^5$ is, or comprises, an RNA sequence. In particular embodiments, $R^5$ is a DNA sequence, $R^4$ is H and $B^P$ an exocyclic amine-protected adenine, an exocyclic amine-protected cytosine, an exocyclic amine-protected guanine, or thymine. In other particular embodiments, $R^5$ is an RNA sequence, $R^4$ is $OR^6$ and $B^P$ is an exocyclic amine-protected adenine, an exocyclic amine-protected cytosine, an exocyclic amine-protected guanine, or uracil.

Certain disclosed exemplary solid support structures within the scope of one or more of the general formulas include:

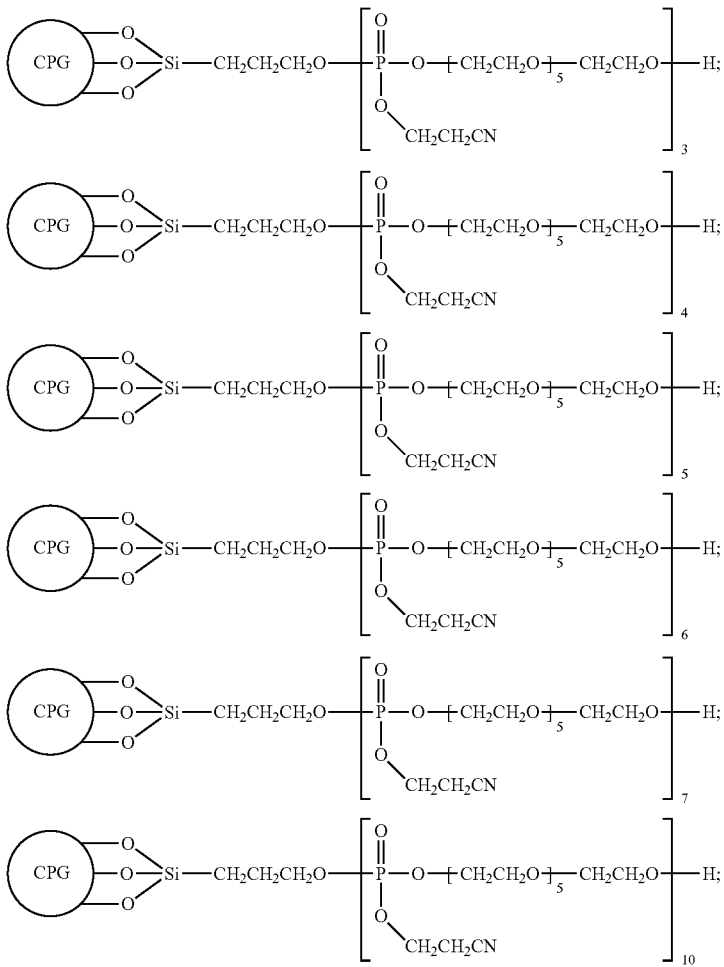

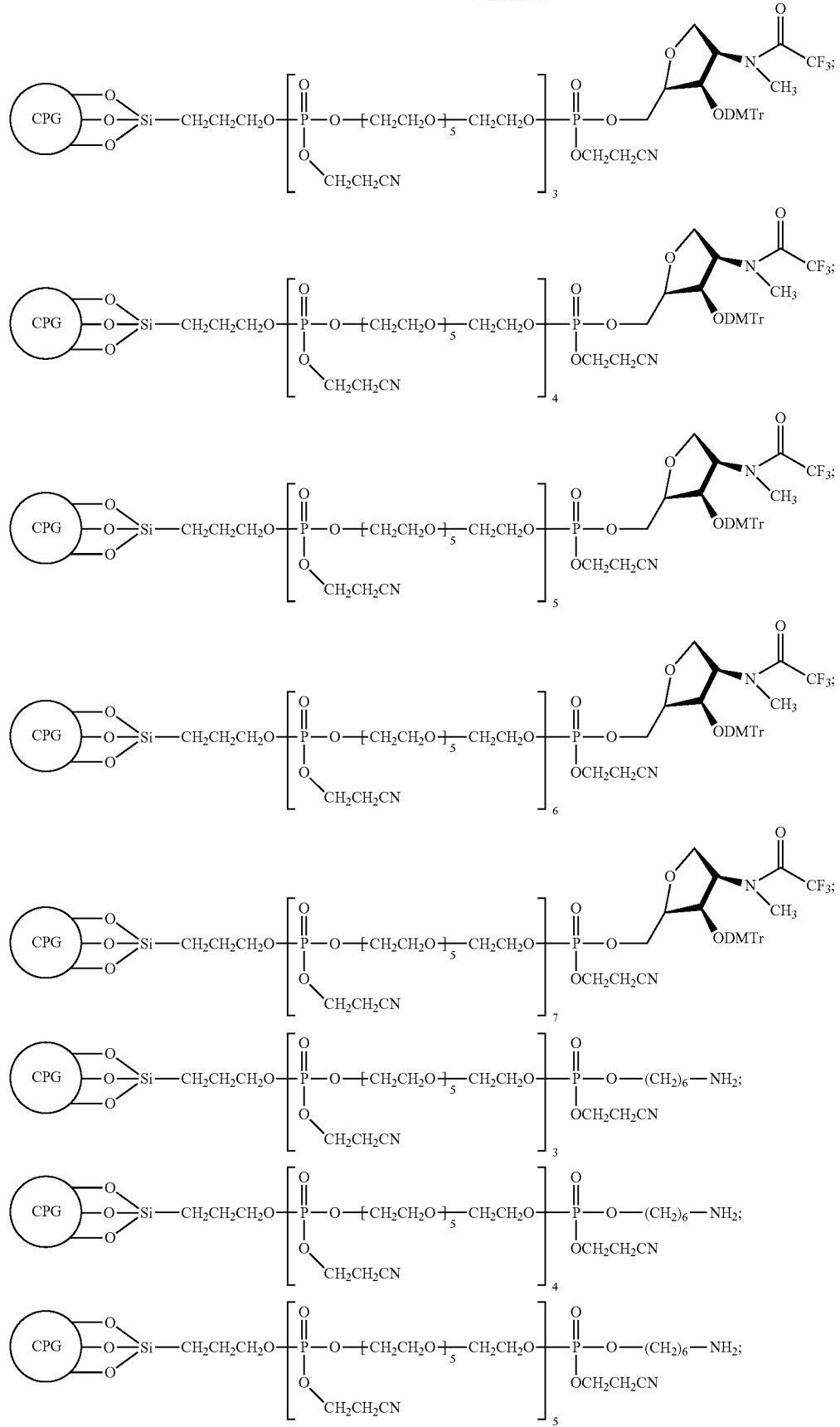

-continued
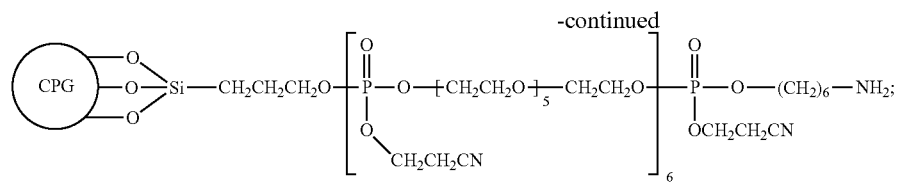
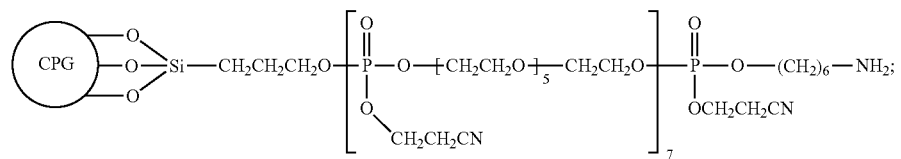
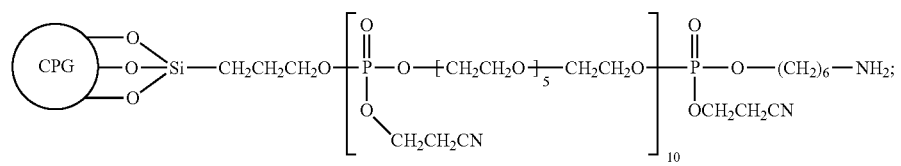
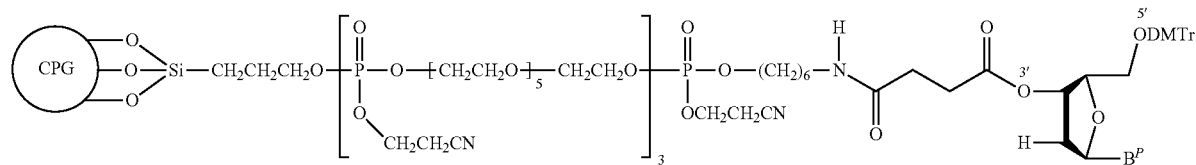
where $B^P$ is an exocyclic amine-protected adenine, an exocyclic amine-protected cytosine, an exocyclic amine-protected guanine, or thymine;
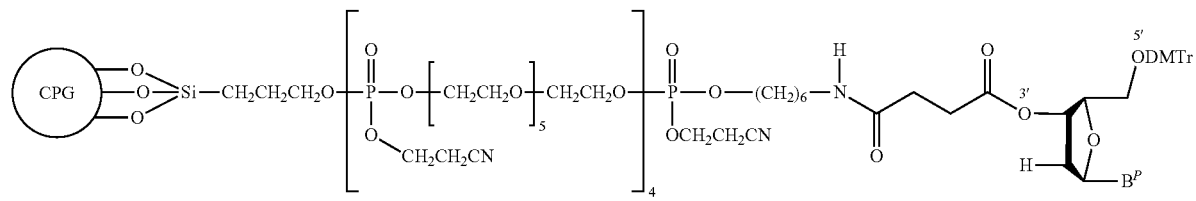
where $B^P$ is an exocyclic amine-protected adenine, an exocyclic amine-protected cytosine, an exocyclic amine-protected guanine, or thymine;
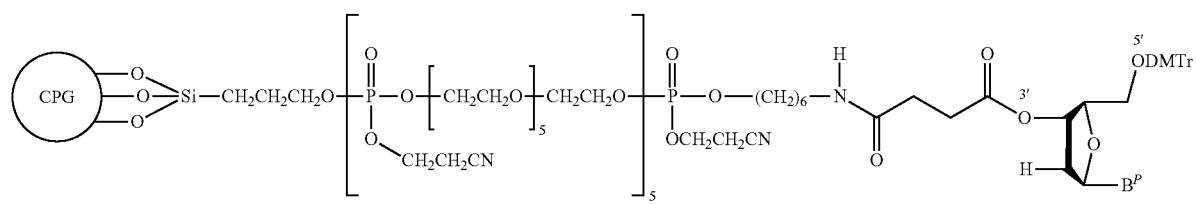

where $B^P$ is an exocyclic amine-protected adenine, an exocyclic amine-protected cytosine, an exocyclic amine-protected guanine, or thymine;

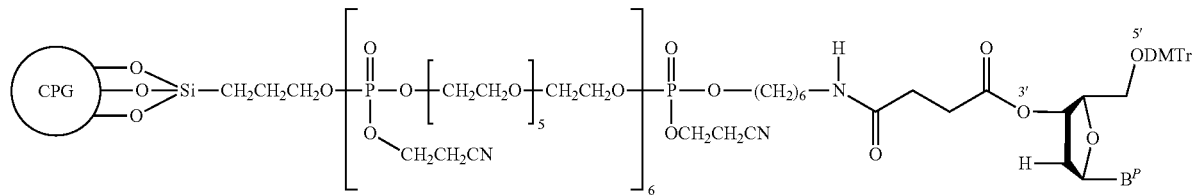

where $B^P$ is an exocyclic amine-protected adenine, an exocyclic amine-protected cytosine, an exocyclic amine-protected guanine, or thymine;

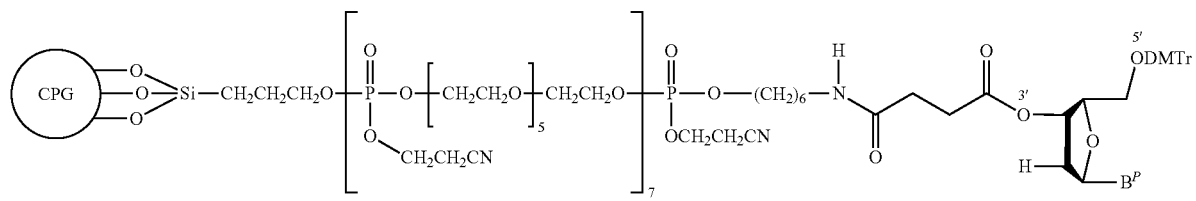

where $B^P$ is an exocyclic amine-protected adenine, an exocyclic amine-protected cytosine, an exocyclic amine-protected guanine, or thymine;

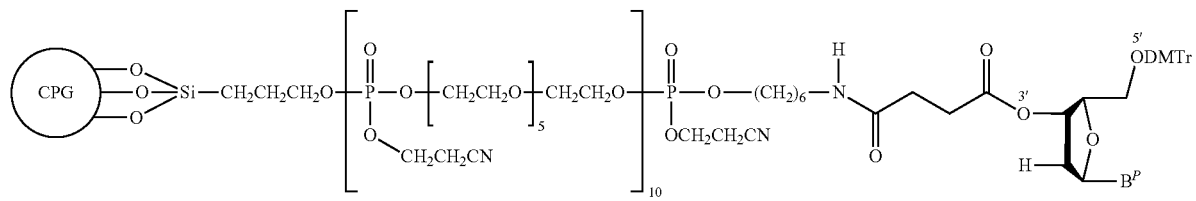

where $B^P$ is an exocyclic amine-protected adenine, an exocyclic amine-protected cytosine, an exocyclic amine-protected guanine, or uracil;

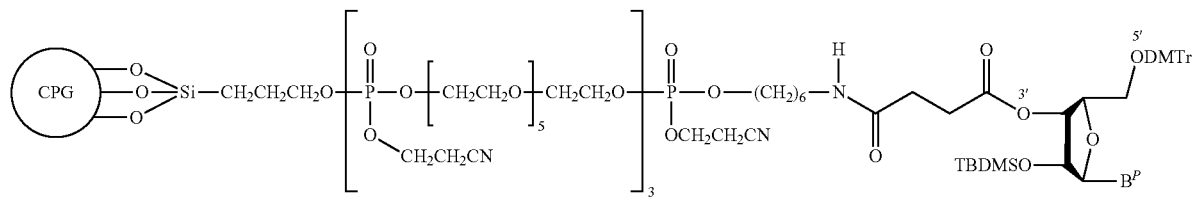

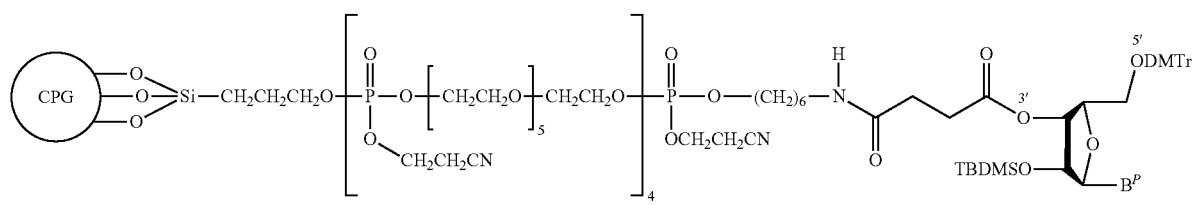

where $B^P$ is an exocyclic amine-protected adenine, an exocyclic amine-protected cytosine, an exocyclic amine-protected guanine, or uracil;

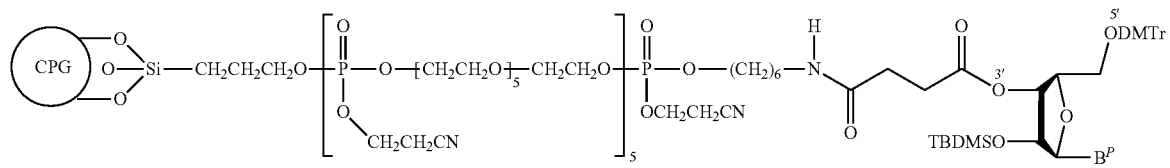

where $B^P$ is an exocyclic amine-protected adenine, an exocyclic amine-protected cytosine, an exocyclic amine-protected guanine, or uracil;

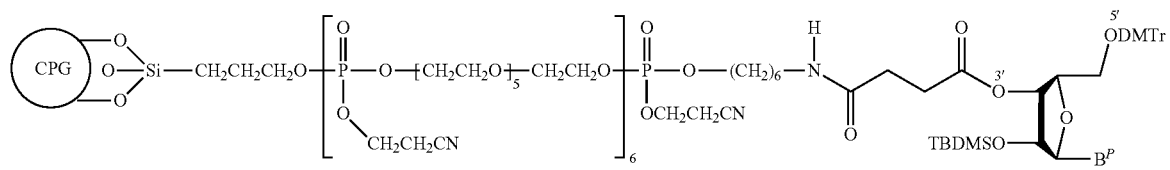

where $B^P$ is an exocyclic amine-protected adenine, an exocyclic amine-protected cytosine, an exocyclic amine-protected guanine, or uracil;

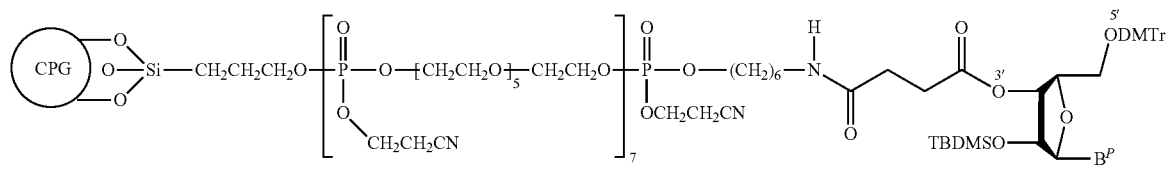

where $B^P$ is an exocyclic amine-protected adenine, an exocyclic amine-protected cytosine, an exocyclic amine-protected guanine, or uracil;

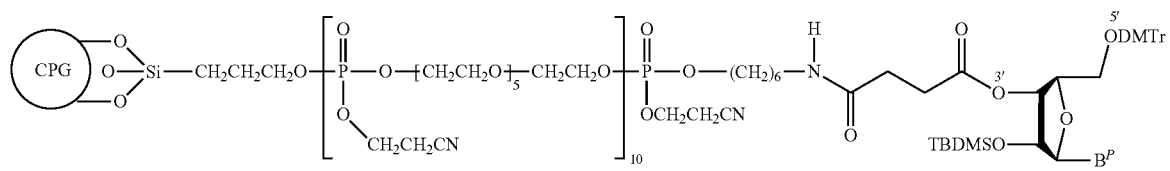

where $B^P$ is an exocyclic amine-protected adenine, an exocyclic amine-protected cytosine, an exocyclic amine-protected guanine, or uracil.

In any embodiments, the loading of the support on the CPG is from greater than zero to 125 µmol/g or more, such as from 5 µmol/g to 125 µmol/g, from 10 µmol/g to 100 µmol/g, or from 15 µmol/g to 75 µmol/g.

III. Method for Making the Solid Support Structure

The disclosed solid support structures can be prepared as exemplified below, as illustrated for specific supports in the examples, and as will be understood by a person of ordinary skill in the art of organic synthesis. An exemplary synthesis may include the following first reaction step according to Scheme 1.

Scheme 1

CPG—OH, OH, OH  $\xrightarrow{(MeO)_3Si(CH_2)_mOAc}$

A

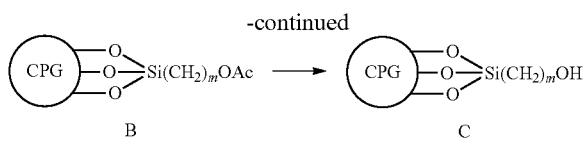

B → C

CPG A is treated with a trialkoxysilane, such as trimethoxysilane as illustrated in Scheme 1, in a suitable solvent, such as an aprotic solvent, for example, toluene. The mixture is agitated, such as by stirring or shaking, at a temperature suitable to facilitate production of compound B. The temperature may be from 20° C. or lower, to 100° C. or more, such as from 25° C. to 75° C. or from 40° C. to 60° C., and in some embodiments, a temperature of about 50° C. is used. The reaction may proceed until the reaction is complete, such as by reaching an equilibrium, and may proceed for from 6 hours to 48 hours, from 12 hours to 36 hours, or from 18 hours to 30 hours, and in some embodiments, the reaction proceeds for about 24 hours. Compound B is then treated with a suitable base, such as aqueous ammonia, to form compound C. The mixture is agitated, such as by stirring or shaking, at a temperature suitable to facilitate the reaction, such as from 25° C. or less to 75° C. or more, or from 40° C. to 60° C., and in some embodiments, a temperature of about 55° C. is used. The reaction may proceed from greater than zero to 6 hours or more, such as from 1 hour to 4 hours, or for about 2 hours. Compound C is then isolated by a suitable technique, such as filtration.

A second reaction step in the exemplary synthesis is provided below according to Scheme 2.

Compound C is treated with phosphoramidite D under a standard solid-phase DNA synthesis protocol, such as conditions recommended by a manufacturer of an automated DNA/RNA synthesizer, to form Compound E. The protecting group is any protecting group suitable to facilitate solid phase DNA synthesis, such as DMTr. And each alkyl group in the (alkyl)$_2$N moiety in phosphoramidite D may be $C_{1-6}$alkyl or the two alkyl moieties together with the nitrogen to which they are attached form a 5- to 7 membered heterocycloaliphatic group. Suitable (alkyl)$_2$N moieties include, but are not limited to, dimethylamino (NCH$_3$)$_2$, diethylamino (N(CH$_2$CH$_3$)$_2$), di-n-propylamino, diisopropylamino, di-n-butylamino, diisopropylamino, diisobutylamino, di-sec-butylamino, di-tert-butylamino, di-n-hexylamino, or morpholino.

Compound E is exposed to an aqueous solution of iodine and then to reagents needed to inactivate any unreacted hydroxyl groups, such as a 1:1 (v/v) solution of Cap A (Ac$_2$O/THF/pyridine) and Cap B (10% 1-Methylimidazole in THF). The protecting group is then removed under acidic conditions to form Compound F. A person of ordinary skill in the art understands the conditions required to remove a particular protecting group, and additional information concerning suitable protecting groups and how to remove them can be found in "Greene's Protective Groups in Organic Synthesis, Fourth Edition," published by John Wiley and Sons, Inc, Apr. 10, 2006. For example, a DMTr protecting group may be removed by treatment with 3% trichloroacetic acid in a suitable solvent, such as a chlorinated solvent (for example, chloroform or dichloromethane).

The chain length can be extended as desired by repeating the steps above, as illustrated in Scheme 3.

Scheme 3

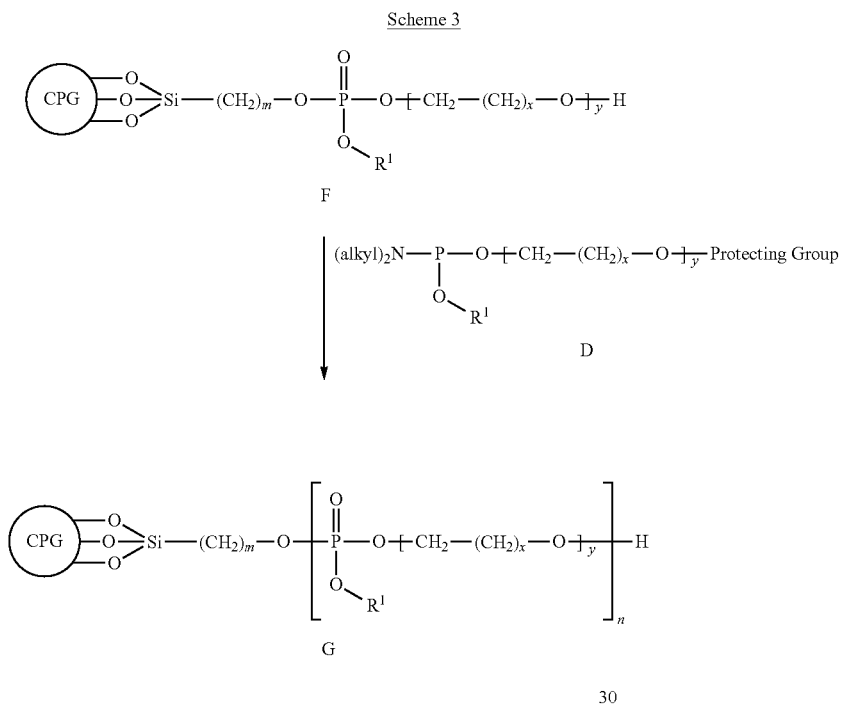

A third reaction step in the exemplary synthesis is provided below according to Scheme 4.

Scheme 4

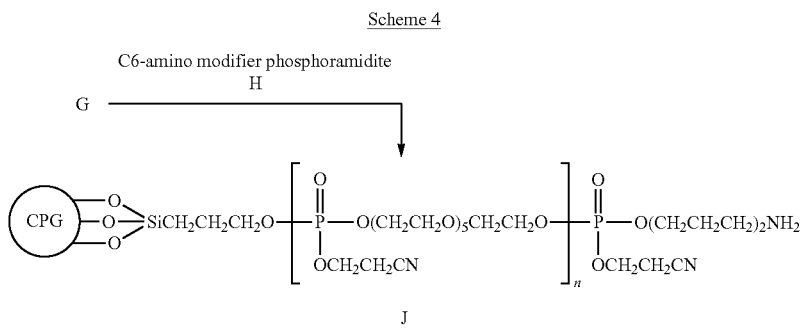

Compound G is obtained after oxidation of the phosphite triester intermediate with an aqueous solution of iodine followed by treatment with a 1:1 (v/v) Cap A:Cap B solution to inactivate unreacted hydroxyl groups and after removal of the protecting group under acidic conditions as previously described with respect to Scheme 2. Compound G is then treated with phosphoramidite H according to standard solid-phase DNA synthesis protocols. Typically, the amino moiety is protected by a suitable protecting group, such as a 4-monomethoxytrityl group. Removal of such a group produces Compound J. A person of ordinary skill in the art understands how to remove such protecting groups. For example, a 4-monomethoxytrityl amino protecting group may be removed using 3% trichloroacetic acid (TCA) in a chlorinated solvent, such as dichloromethane, over a period of 15 minutes at about 25° C.

A fourth reaction step in the exemplary synthesis is provided below according to Scheme 5.

Scheme 5

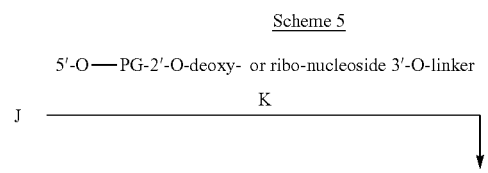

-continued

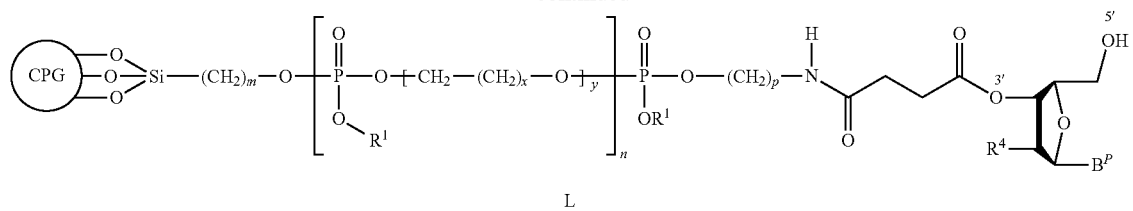

L

Compound J is treated with a suitable 5'-O-deoxy- or ribonucleoside K comprising a nucleic acid base suitable for the 3'-end of the resultant nucleic acid sequence, and a linker suitable to attach the nucleoside to the solid support. A person of ordinary skill in the art understands that if the nucleic acid comprises an exocyclic amine, such amine likely will be protected by a suitable protecting group, such as a protecting group disclosed herein. In Scheme 5, an exemplary succinate linker is shown, but a person of ordinary skill in the art understands that any linker suitable to facilitate the DNA or RNA sequence synthesis may be used. The reaction proceeds in the presence of a suitable coupling agent, such as dicyclohexylcarbodiimide (DCC), ethyl-(N', N'-dimethylamino)propylcarbodiimide hydrochloride (EDC), diisopropylcarbodiimide (DIC), carbonyldiimidazole (CDI), BOP, PyBOP, BOP-Cl, or HATU. The reaction is performed in a solvent suitable to facilitate the coupling reaction, such as pyridine, DMF, acetonitrile, toluene, a chlorinated solvent, such as chloroform, dichloromethane, or dichloroethane, or any combination thereof. Pyridine may be used in combination with a solvent to further facilitate the reaction proceeding.

After the reaction is complete, the reaction mixture is treated with a 1:1 (v/v) Cap A:Cap B solution to inactivate any unreacted amines moieties, and the solid support is filtered and treated with a suitable reagent, such as TCA in a chlorinated solvent, such as dichloromethane, to remove the protecting group to form compound L.

An alternative exemplary synthesis to those illustrated by Schemes 4 and 5 is shown in Scheme 6.

Scheme 6

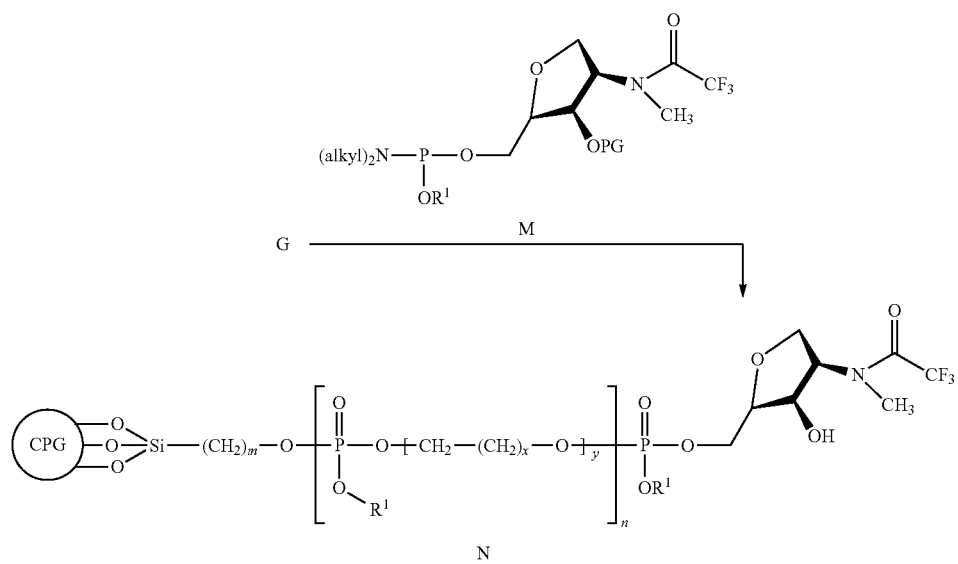

Compound G is treated with phosphoramidite M according to standard solid-phase DNA synthesis protocols. After treatment with an aqueous solution of iodine, unreacted hydroxyl groups are inactivated by a 1:1 (v/v) Cap A:Cap B solution as previously described with respect to Scheme 2. Typically, the hydroxyl moiety of M is protected by a suitable protecting group, such as a 4-monomethoxytrityl or 4,4'-dimethoxytrityl group. Removal of such a group produces Compound N, and a person of ordinary skill in the art understands the conditions used to remove such protecting groups. For example, a 4-monomethoxytrityl or 4,4'-dimethoxytrityl hydroxyl protecting group may be removed using 3% TCA in a chlorinated solvent, such as dichloromethane, over a period of 15 minutes at about 25° C.

In some embodiments, phosphoramidite M is

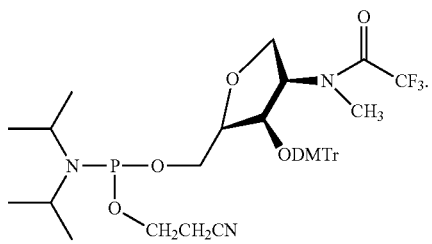

Using either solid support L or solid support N, the DNA or RNA sequence can be synthesized in an automated DNA/RNA synthesizer using the standard protocols recommended by the manufacturer. Upon completion of the automated solid-phase synthesis, the DNA sequence is released by passing ammonium hydroxide through the synthesis column over a suitable period, such as from greater than zero to 1 hour or more, or from 10 minutes to 30 minutes, while collecting the eluate. The eluate then is heated to a temperature suitable to ensure complete deprotection, such as from 30° C. or less to 100° C. or less, for example, from 40° C. to 75° C. or from 50° C. to 60° C., and in some embodiments, the temperature is about 55° C. The eluate is heated for a time period to facilitate deprotection, such as from 6 hours or less to 30 hours or more, from 12 hours to 24 hours, or from 15 hours to 20 hours, and in some embodiments, the eluate is heated for about 18 hours.

Alternatively, nucleic acid sequences, such as RNA sequences, may be manually released by suspending each support in an alcoholic solution of concentrated ammonium hydroxide, typically an ethanolic solution, at an approximate ratio of from 1:1 v/v to 1:5 or more v/v, such as about EtOH:NH$_4$OH (1:3 v/v). The mixture is maintained, typically in a closed container, at ambient temperature, such as from 20° C. to 30° C. or about 25° C., for a time period suitable to facilitate release of the nucleic acid sequence. The time period may be from 6 hours or less to 24 hours or more, such as from 12 hours to 18 hours, and in some embodiments, the time period is about 16 hours. The support is then filtered and washed with RNase free water. The filtrates are concentrated to dryness, such as by centrifugation and/or a speedvac concentrator. For RNA sequences, the residue is dissolved in a suitable solvent, such as DMSO, and treated with conditions suitable to remove the OH protecting group. In some embodiments, the OH protecting group is fluoride-labile, and the residue is treated with a fluoride reagent, such as triethylamine trihydrofluoride. The mixtures are heated, such as on a heat block, at a temperature suitable to facilitate OH deprotection, such as from 50° C. or less to 100° C. or more, from 55° C. to 75° C. or about 65° C. for a suitable time period, such as from 1 hours or less to 56 hours or more, from 2 hours to 4 hours or about 3 hours.

IV. Examples

Example 1

Preparation of the 3-hydroxypropylated CPG Support 3

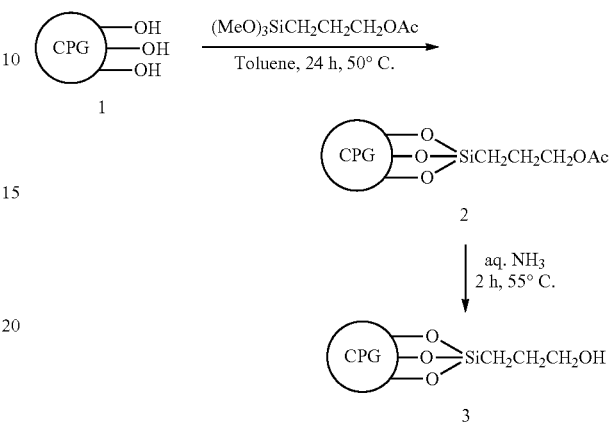

To CPG (500 Å, 1.00 g, 1) placed in a 4-mL screw-capped glass vial was added a solution of 3-acetoxypropyltrimethoxysilane (890 mg, 4.00 mmol) in dry toluene (4 mL). The suspension was then shaken at 50° C. over a period of 24 hours. The 3-acetoxypropylated support 2 was filtered, washed with acetonitrile (10 mL), air-dried and transferred to a 7-mL screw-capped glass vial. Concentrated aqueous ammonia (4 mL) was added to the vial which was immediately capped; the suspension was shaken at 55° C. over 2 hours. The 3-hydroxypropylated support 3 was filtered and successively washed with water (10 mL), acetonitrile (10 mL), air dried and then left under high vacuum for 1 hour at about 25° C.

Example 2

Conversion of the CPG Support 3 to CPG Supports 5 and 6

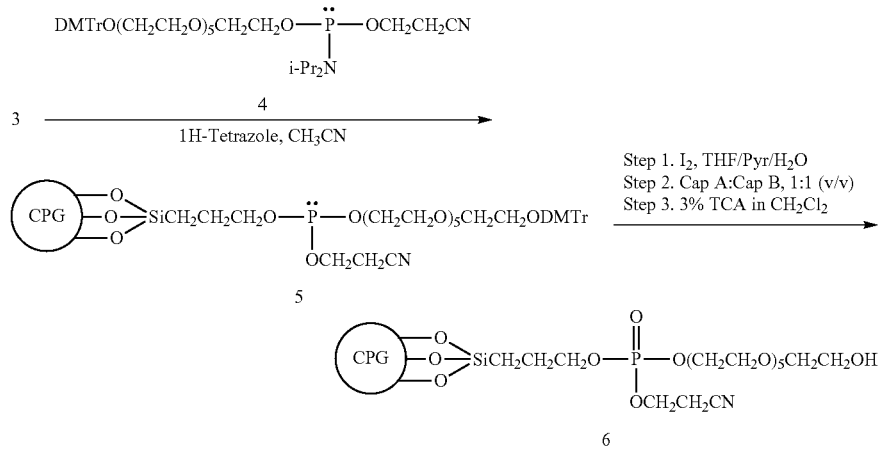

A 0.1 M solution of commercial phosphoramidite 4 in anhydrous CH$_3$CN was employed for the phosphitylation of CPG support 3, which was performed via a standard 1 µmole scale solid-phase DNA synthesis protocol under conditions recommended by the manufacturer of the automated DNA/RNA synthesizer. The CPG support 5 was then exposed to an aqueous solution of iodine followed by a 1:1 (v/v) solution of Cap A (Ac$_2$O/THF/pyridine) and Cap B (10% 1-methylimidazole in THF) to inactivate unreacted hydroxyls. The CPG support 6 was produced upon exposing 5 to a solution of 3% trichloroacetic acid (TCA) in CH$_2$Cl$_2$ to cleave the 4,4'-dimethoxytrityl (DMTr) group according to a standard automated DNA synthesis protocol. The released DMTr cation solution, obtained from an accurately weighed sample of support 5, was collected into a 10-mL volumetric flask and spectrophotometrically measured at 498 nm to reveal a functional hydroxyl concentration of 108 µmole OH/gram of CPG support 6.

Example 3

General Procedure for the Automated Preparation of CPG Supports 7, 8 or 9

6 →(Repeat coupling reaction with 4 followed by steps 1 through 3, two, four or six times)

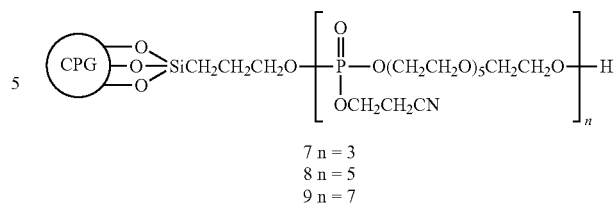

7 n = 3
8 n = 5
9 n = 7

The procedure comprises repeating all the steps described above at the same scale, under the same conditions, using CPG support 6 as the starting material.

Example 4

Typical Procedure for the Automated Preparation of CPG Supports 10, 11 or 12

7 n = 3
8 n = 5
9 n = 7

C6-amino modifier phosphoramidite, 1H-tetrazole, CH$_3$CN, followed by steps 1 through 3 from Example 2

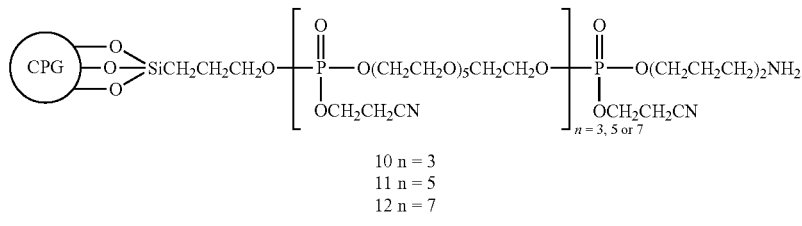

10 n = 3
11 n = 5
12 n = 7

A 0.1 M solution of commercial 6-(4-monomethoxytritylamino)hexyl-(2-cyanoethyl)-(N,N-diisopropyl)-phosphoramidite in anhydrous CH$_3$CN was employed for the phosphitylation of CPG support 7, 8 or 9, at the 1 µmole scale, according to a standard solid-phase DNA synthesis protocol. The CPG support 10, 11, or 12, was then treated with an aqueous solution of iodine followed by a 1:1 (v/v) Cap A:Cap B solution to inactivate unreacted hydroxyls. Cleavage of the 4-monomethoxytritylamino protecting group was performed manually, off the automated DNA/RNA synthesizer, using 3% TCA in CH$_2$Cl$_2$ over a period of 15 min at about 25° C. Multiple batches of each CPG support were needed to generate enough material to initiate solid-phase synthesis of each DNA or RNA sequence at the 1 µmole scale on each support.

Example 5

General Procedure for the Preparation of CPG Supports 13, 14 or 15

10 n = 3
11 n = 5
12 n = 7

5'-O—DMTr-2'-O-deoxy- or ribo-nucleoside 3'-O-succinate
DCC, Pyr:DMF (9:1 v/v), CH$_2$Cl$_2$, 24 h, 25° C.

-continued

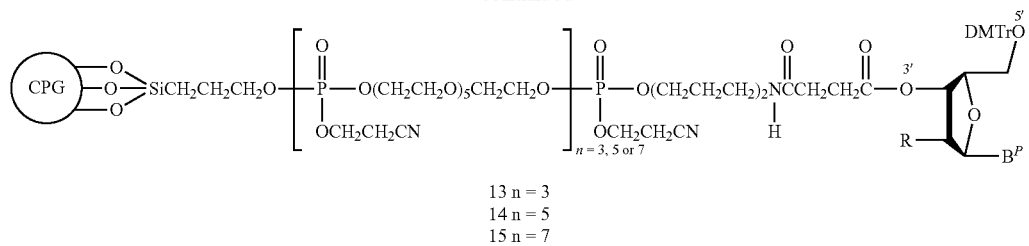

13 n = 3
14 n = 5
15 n = 7

To a flame-dried 4-mL glass vial was added CPG support 10, 11 or 12 (50 mg) and a 5'-O-(4,4'-dimethoxytrityl)-2'-deoxythymidine-3'-O-succinate, N$^4$-benzoyl-5'-O-(4,4'-dimethoxytrityl)-2'-deoxycytidine-3'-O-succinate, N$^6$-benzoyl-5'-O-(4,4'-dimethoxytrityl)-2'-deoxyadenosine-3'-O-succinate, N$^2$-isobutyryl-5'-O-(4,4'-dime-thoxytrityl)-2'-deoxyguanosine-3'-O-succinate or 5'-O-(4,4'-dimethoxytrityl)-2'-O-tert-butyldimethylsilyl uridine-3'-O-succinate salt (30 mg) along with N,N'-dicyclohexylcarbodiimide (15 mg). The glass vial and its content were then subjected to high vacuum for 2 hours at about 25° C. A solution of 10% dry pyridine in anhydrous DMF (200 µL) was added by syringe to the glass vial, which was immediately sealed with a teflon-lined screw cap and shaken at about 25° C. over a period of 24 hours. The suspension was filtered, washed with dry CH$_3$CN (10 mL) and treated with 2-mL of a 1:1 (v/v) Cap A:Cap B solution to inactivate any unreacted amine functions. The CPG support was again filtered, washed with dry CH$_3$CN (10 mL) and air-dried. An accurately weighed sample of support 13, 14 or 15 was mixed with a solution of 3% TCA in CH$_2$Cl$_2$ (10 mL), over 5 minutes at about 25° C., to spectrophotometrically measure at 498 nm the concentration of the leader nucleoside (dA$^{Bz}$) covalently linked to the support. DMTr cation measurements revealed a 5'-hydroxyl concentration of: 57 µmole/gram of CPG support 13; 43 µmole/gram of CPG support 14 or 26 µmole/gram of CPG support 15. When the leader nucleoside is dT, dC$^{Bz}$, dG$^{iBu}$ or U, DMTr cation measurements were: 51 µmole/gram, 49 µmole/gram, 50 µmole/gram or 49 µmole/gram of CPG support 14, respectively.

Example 6

Protocol for Automated Synthesis of DNA or RNA Sequences on Commercial LCAA-CPG and CPG Supports 13, 14 and 15

13 n = 3
14 n = 5
15 n = 7

1. Cap A:Cap B, 1:1 (v/v)
2. 3% TCA in CH$_2$Cl$_2$
3. Standard solid-phase DNA synthesis

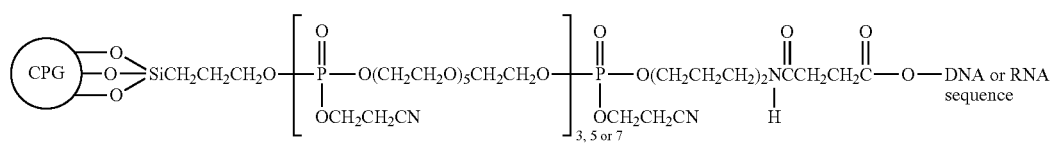

16 n = 3
17 n = 5
18 n = 7

Automated syntheses of DNA and RNA sequences were performed on a DNA/RNA synthesizer, employing commercial long chain alkylamine controlled-pore glass supports (LCAA-CPG) or modified CPG supports 13, 14 and 15 pre-loaded with suitably protected leader deoxy- or ribonucleosides. Each solid support was accurately weighed, based on its leader nucleoside load, to provide one micromole of leader nucleoside per synthesis column. The synthesis of DNA or RNA sequences was conducted, side-by-side, on LCAA-CPG and CPG support 13 according to the standard (trityl-off) DNA or RNA protocol conditions recommended by the manufacturer of the DNA/RNA synthesizer. Side-by-side syntheses were carried out on the same day by the same operator, using the same batches of deoxy- or ribonucleoside phosphoramidites under identical conditions in terms of concentration, activation/coupling times and subsequent usage of reagents through all the steps of each synthesis cycle. This protocol was repeated under identical conditions for the side-by-side synthesis of DNA sequences on LCAA-CPG and CPG support 14 and 15.

Example 7

Deprotection of the DNA or RNA Sequences Released from LCAA-CPG and CPG Supports 16, 17 and 18

16 n = 3
17 n = 5
18 n = 7

↓ Deprotection and release of the DNA or RNA sequences from the solid supports

5'-d(CTGAGTAGCGAACGTGAAGA) from CPG supports 16, 17 and 18
5'-d(ATAGTGTGCATCGATGCCAC)
5'-d(CTCTGTACCTTACGTCTTCG)
5'-d(TCTTGGTTACATGAAATCCT)          each from CPG support 17
5'-r(UCUUGGUUACAUGAAAUCCU)

+ shorter than full length DNA or RNA sequences

Upon completion of the automated solid-phase synthesis of DNA or RNA sequences, the synthesis columns containing the DNA sequences linked to LCAA-CPG support and CPG supports 16, 17 or 18 were taken off the DNA/RNA synthesizer, and each DNA sequence of each CPG support was manually released by passing concentrated ammonium hydroxide (1 mL) through the synthesis column over a period of 15 minutes while collecting the eluate in a 4-mL screw cap glass vial. Each glass vial was then capped and heated at 55° C. for 18 hours on a heat block to ensure complete deprotection. The ammoniacal solution of each DNA sequence was then concentrated to about 50% of its original volume using a stream of air to remove most of the ammonia from each solution.

The synthesis columns containing the RNA sequence linked to LCAA-CPG and CPG 17 supports was manually released upon suspending each support in 1 mL of an ethanolic solution of concentrated ammonium hydroxide [EtOH:NH$_4$OH (1:3 v/v)] kept in capped 4-mL screw cap glass vials over 16 hours at about 25° C. The support of each vial was then filtered and washed with RNase free water (0.5 mL) twice, and the filtrates were placed in 1.5 mL polypropylene microcentrifuge tubes and concentrated to dryness using a speedvac concentrator. Each RNA sequence was dissolved in DMSO (100 µL) to which was added triethylamine trihydrofluoride (125 The solutions were heated on a heat block at 65° C. for 3 hours. Each deprotected RNA sequence solution was cooled to room temperature, diluted with 775 µL of RNase free water, and desalted through a PD-10 column. Each desalted RNA solution was immediately analyzed by RP-HPLC as described below.

The identity of all nucleic acid sequences released from the CPG support 17 was verified by mass spectrometry.

MALDI: m/z calcd for $C_{197}H_{244}N_{85}O_{114}$-$P_{19}$:
6215 [M + H]$^+$; found: 6212.
(SEQ ID NO: 1):
5'-d(CTGAGTAGC-GAACGTGAAGA)

MALDI: m/z calcd for $C_{196}H_{249}N_{68}O_{121}P_{19}$:
6082 [M + H]$^+$; found: 6077.
(SEQ ID NO: 2):
5'-d(TCTTGGTTACAGA-AATCCT)

MALDI: m/z calcd for $C_{193}H_{249}N_{62}O_{124}P_{19}$:
6010 [M + H]$^+$; found: 6014.
(SEQ ID NO: 4):
5'-d(CTCTGTACCTTACGTCTTCG)

MALDI: m/z calcd for $C_{195}H_{246}N_{75}O_{118}P_{19}$:
[M + H]$^+$; 6117; found: 6118.
(SEQ ID NO: 5):
5'-d(ATAGTGTGCATCGATGCCAC)

MALDI: m/z calcd for $C_{188}H_{233}N_{68}O_{141}P_{19}$:
[M + H]$^+$; 6290; found: 6282.
(SEQ ID NO: 3):
5'-r(UCUUGGUUACAUGAAAUCCU)

Example 8

Comparative RP-HPLC Analyses of Unpurified DNA or RNA Sequences Released from LCAA-CPG and CPG Supports 16, 17 and 18

All analyses were performed using an Agilent Technologies 1260 Infinity II HPLC system equipped with a diode array detector for spectral analysis. The OpenLAB CDS ChemStation software provides peak integration capabilities needed for comparative analyses. Optimally, 0.2 OD$_{260}$ unit of fully deprotected and unpurified DNA or RNA sequences released from the above CPG supports were each analyzed using an Agilent ion-pair reversed-phase AdvanceBio Oligonucleotide column under the following chromatographic conditions: from 0.1 M triethylammonium acetate (pH 7.0), a linear gradient of 0.66% CH$_3$CN/min is pumped at a flow rate of 0.8 mL/min for 30 minutes. Chromatographic peak areas were measured using the OpenLAB CDS ChemStation software by perpendicularly extending the start and end of DNA or RNA peak elution points to base line.

Example 9

Results and Discussion

In this study, a controlled-pore glass support functionalized with multiple hexaethylene glycol spacers was designed, implemented and demonstrated to reduce the level of process-related impurities in synthetic DNA and RNA sequences when compared to that achieved using commercial long-chain alkylamine controlled-pore glass supports (also see Grajkowski et al., Bioorg. Med. Chem. 28:115779, 2020, herein incorporated by reference in its entirety).

A first attempt to reduce the level of process-related impurities in synthetic DNA and RNA sequences used a CPG 500 support functionalized with one hexaethylene glycol spacer under typical solid-phase synthesis conditions. A DNA sequence (20-mer) was produced in a yield not better than that obtained (86%) when employing the standard commercial LCAA-CPG support. Hexaethylene glycol has about the same number of carbon-carbon (C—C) bond lengths (about 18) than that of the long chain alkylamine spacer of LCAA-CPG.

It was hypothesized that a CPG support functionalized with either a spacer much larger in length than the alkylamine spacer of LCAA-CPG or multiple hexaethylene glycol spacers would improve access of activated phosphoramidites and required reagents to the leader nucleoside for efficient initiation of solid-phase DNA or RNA synthesis. Therefore, the CPG support 6 (see Example 2) was functionalized with two, four and six additional hexaethylene glycol spacers to provide the CPG supports 13, 14 and 15 from which, solid-phase syntheses of DNA and RNA sequences were conducted to provide supports 16, 17, and 18, respectively. The quality of the nucleic acid sequences obtained from these CPG supports was assessed by HPLC and compared with that obtained from the same sequences made from the commercial LCAA-CPG support. FIG. 1 provides expanded HPLC profiles of unpurified 5'-d(CTGAGTAGCGAACGTGAAGA) (SEQ ID NO: 1), which was released from commercial LCAA-CPG (red profile) or CPG support 16 (blue profile) after complete deprotection. Peak heights of each profile were normalized to the highest peak, which was then set to 0.15 absorbance unit (AU) at 254 nm. FIG. 1 clearly illustrates that the shoulder on the right side of the red profile peak at retention time (rt: 20.3 min) was significantly reduced in the blue profile corresponding to the sequence produced using the disclosed solid support structure (rt: 20.5 min), whereas the red profile peak at 21.7 minutes, that corresponds to the sequence made using the commercial LCAA-CPG support, was essentially absent in the blue profile.

Figure 2:
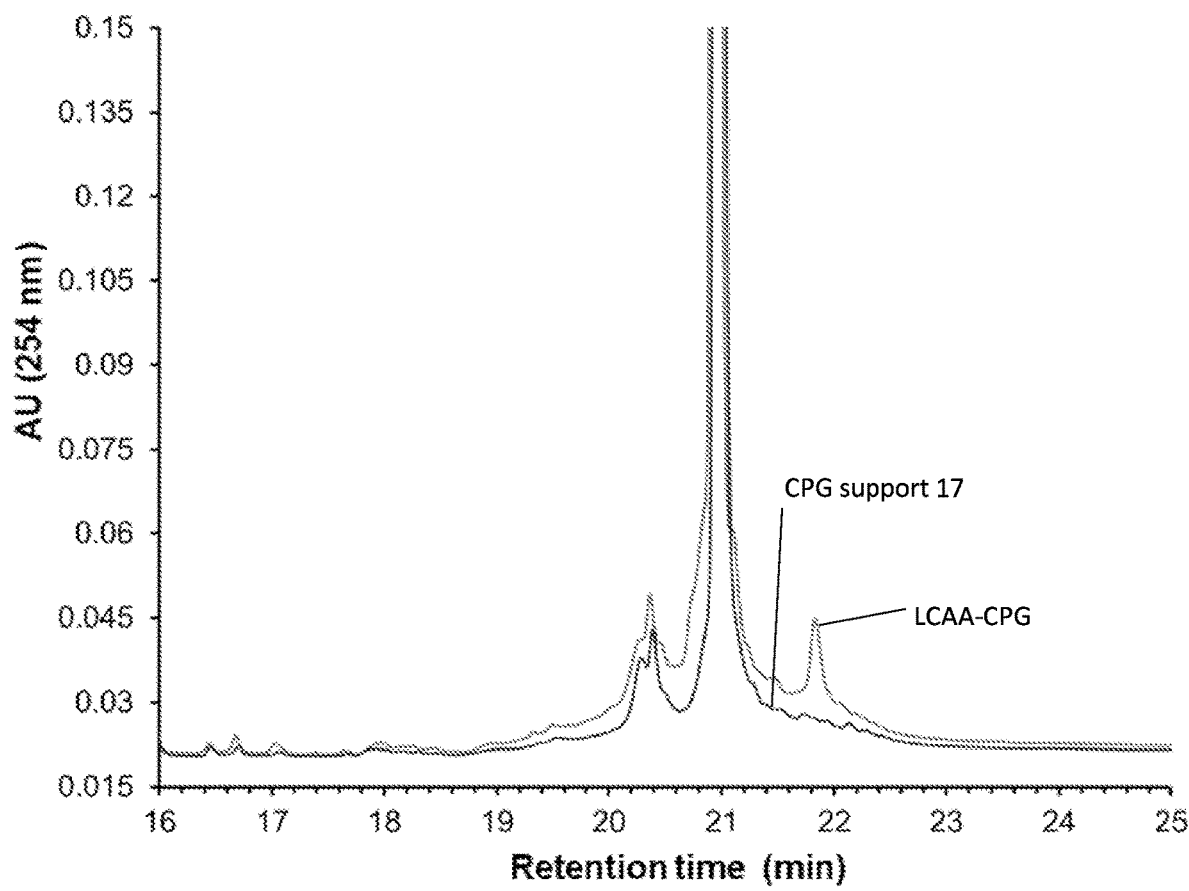
FIG. 2 is a graph of retention time versus absorbance units at 254 nm, illustrating the HPLC profiles of unpurified 5'-d(CTGAGTAGCGAACGTGAAGA) (SEQ ID NO: 1) produced by an embodiment of the disclosed solid support structure comprising 5 hexaethylene glycol phosphate repeating units, and comparing it to the same sequence produced using a commercial LCAA-CPG support.

FIG. 2 provides the expanded HPLC profiles of unpurified SEQ ID NO: 1, which was released from commercial LCAA-CPG (red profile) or CPG support 17 (blue profile) after complete deprotection. Peak heights of each profile were normalized to the highest peak, which was then set to 0.15 absorbance unit (AU) at 254 nm. FIG. 2 demonstrates that the product released from CPG support 17 was of a product of higher quality than that obtained from the commercial LCAA-CPG support. The presence of the shoulder on the right side of the peak shown at rt: 20.4 min and of the peak at 21.8 min in the red profile was considerably reduced in the profile corresponding to CPG support 17. Another notable difference between the profiles provided by FIGS. 1 and 2 was the absence of the relatively large shoulder on the right side of the LCAA-CPG main peak at rt: 21.2 minutes. Furthermore, the shape of the main peak observed in the blue profile of FIG. 2 was much slimmer than that of the red LCAA-CPG profile. Without being bound to a particular theory, this indicated a substantial reduction of process-related impurities superimposed on the main product peak.

Figure 3:
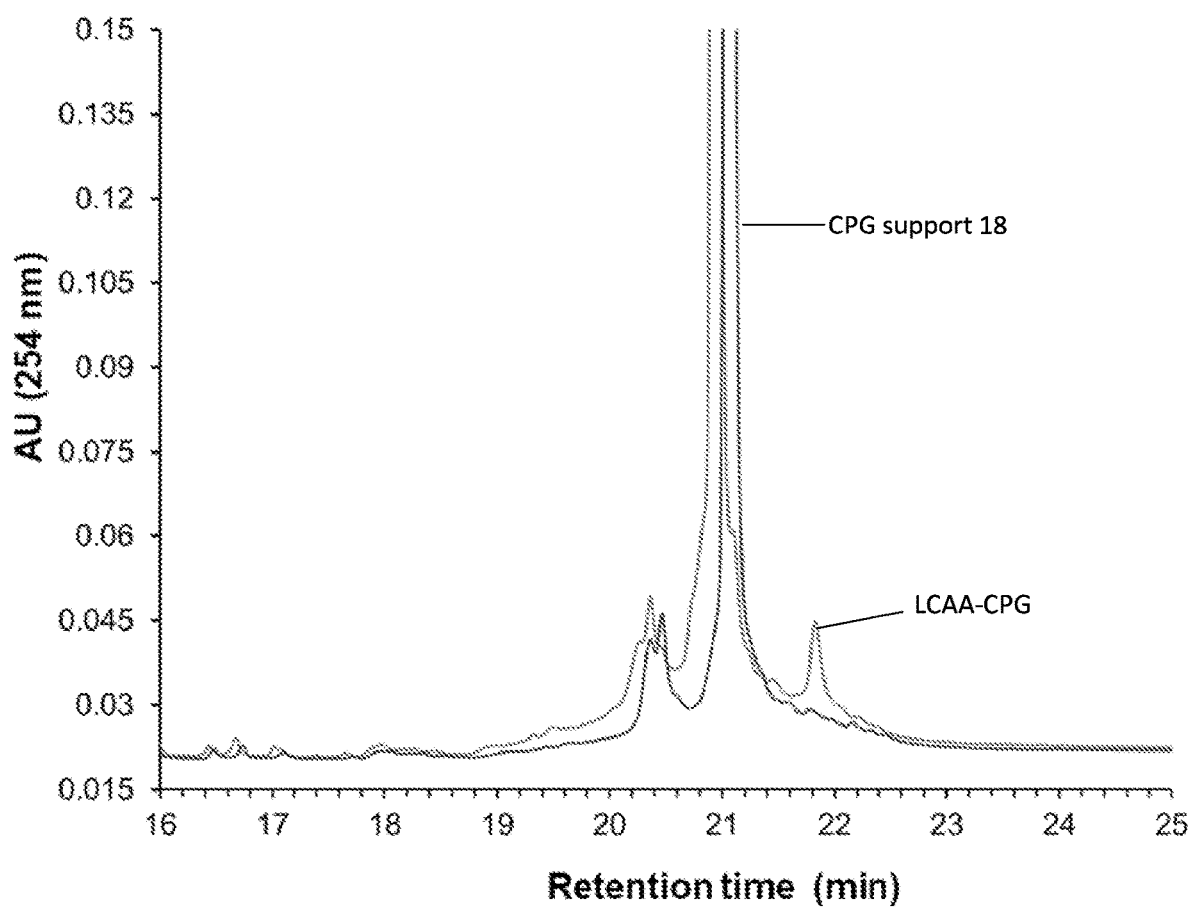
FIG. 3 is a graph of retention time versus absorbance units at 254 nm, illustrating the HPLC profiles of unpurified 5'-d(CTGAGTAGCGAACGTGAAGA) (SEQ ID NO: 1) produced by an embodiment of the disclosed solid support structure comprising 7 hexaethylene glycol phosphate repeating units, and comparing it to the same sequence produced using a commercial LCAA-CPG support.
Figure 4:
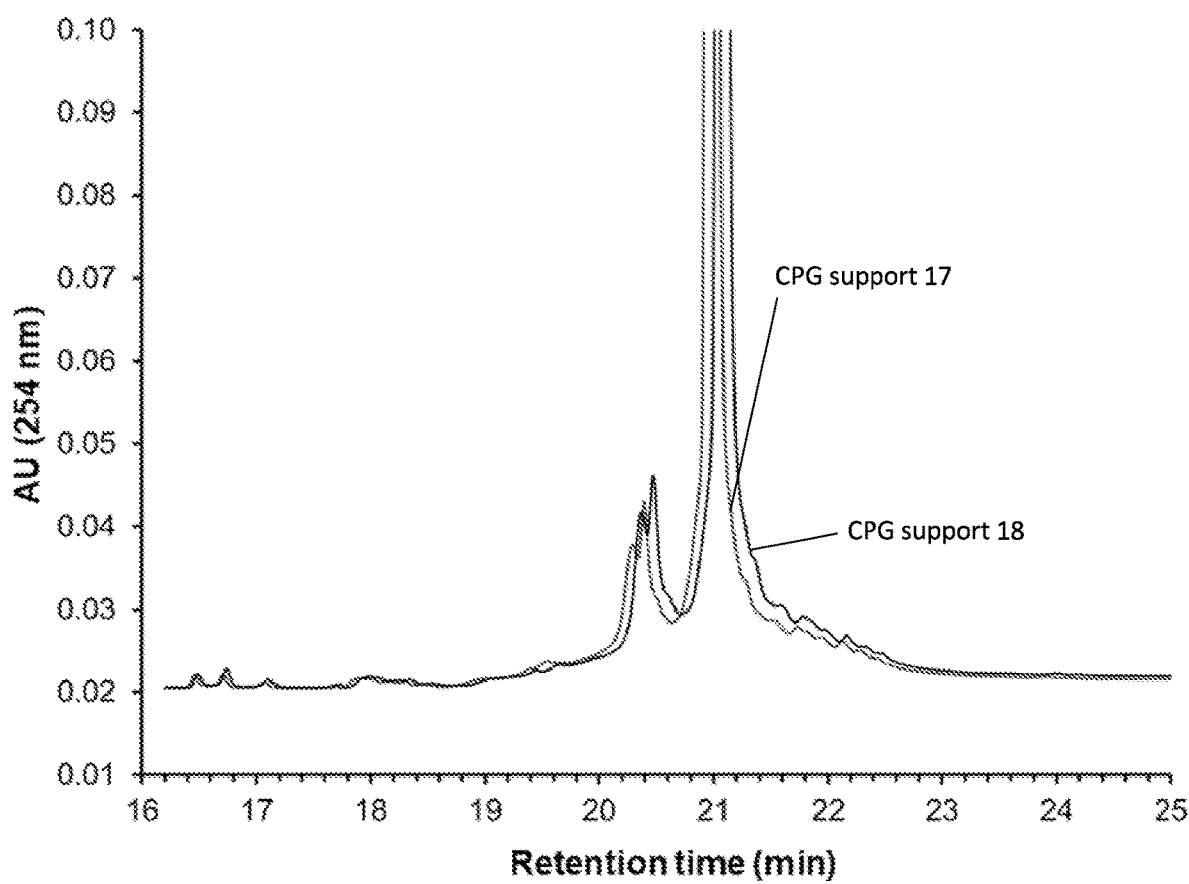
FIG. 4 is a graph of retention time versus absorbance units at 254 nm, comparing the HPLC profiles of unpurified 5'-d(CTGAGTAGCGAACGTGAAGA) (SEQ ID NO: 1) produced by embodiments of the disclosed solid support structure comprising 5 (blue) or 7 (black) hexaethylene glycol phosphate repeating units.

The results obtained by using CPG support 14 prompted an investigation as to whether better results could be obtained using CPG support 15 for solid-phase synthesis of SEQ ID NO: 1. FIG. 3 provides the extended HPLC profiles of unpurified SEQ ID NO: 1 that were released from commercial LCAA-CPG (red) or disclosed CPG support 18 (blue) after complete deprotection. FIG. 4 provides the extended HPLC profiles of unpurified SEQ ID NO: 1 that were released from disclosed CPG support 17 (blue) or support 18 (black) after complete deprotection. For both FIGS. 3 and 4, peak heights of each profile were normalized to the highest peak, which was then set to 0.15 absorbance unit (AU) at 254 nm. FIGS. 3 and 4 show that the release of SEQ ID NO: 1 from CPG support 18 was highly comparable to that obtained from support 17 based on side-by-side comparison of their chromatographic profiles.

Results of the above experiments demonstrated that the disclosed CPG support provided a significant reduction in process-related impurities formation, compared to the commercial LCAA-CPG support, during solid-phase synthesis of nucleic acid sequences.

Figure 5:
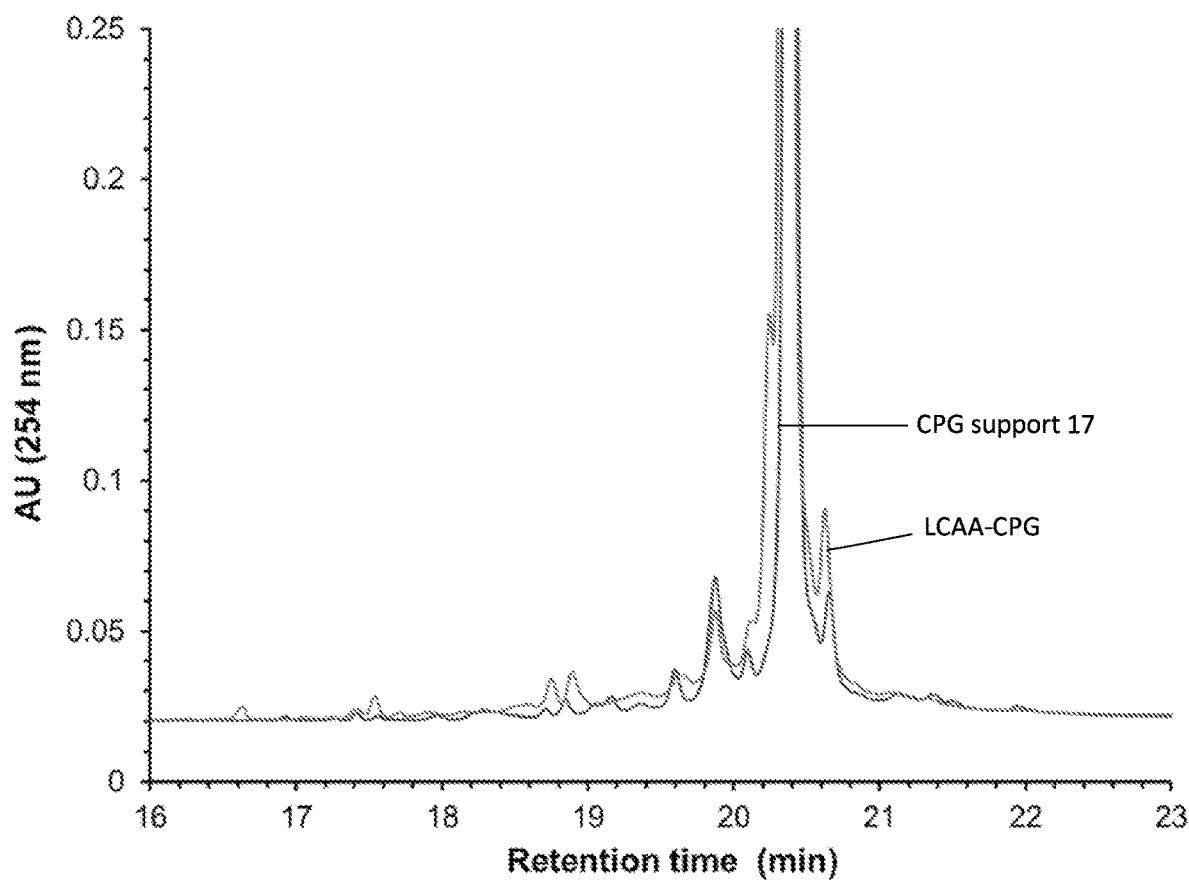
FIG. 5 is a graph of retention time versus absorbance units at 254 nm, illustrating the HPLC profiles of unpurified 5'-r(UCUUGGUUACAUGAAAUCCU) (SEQ ID NO: 3) produced by an embodiment of the disclosed solid support structure comprising 5 hexaethylene glycol phosphate repeating units, and comparing it to the same sequence produced using a commercial LCAA-CPG support.
Figure 6:
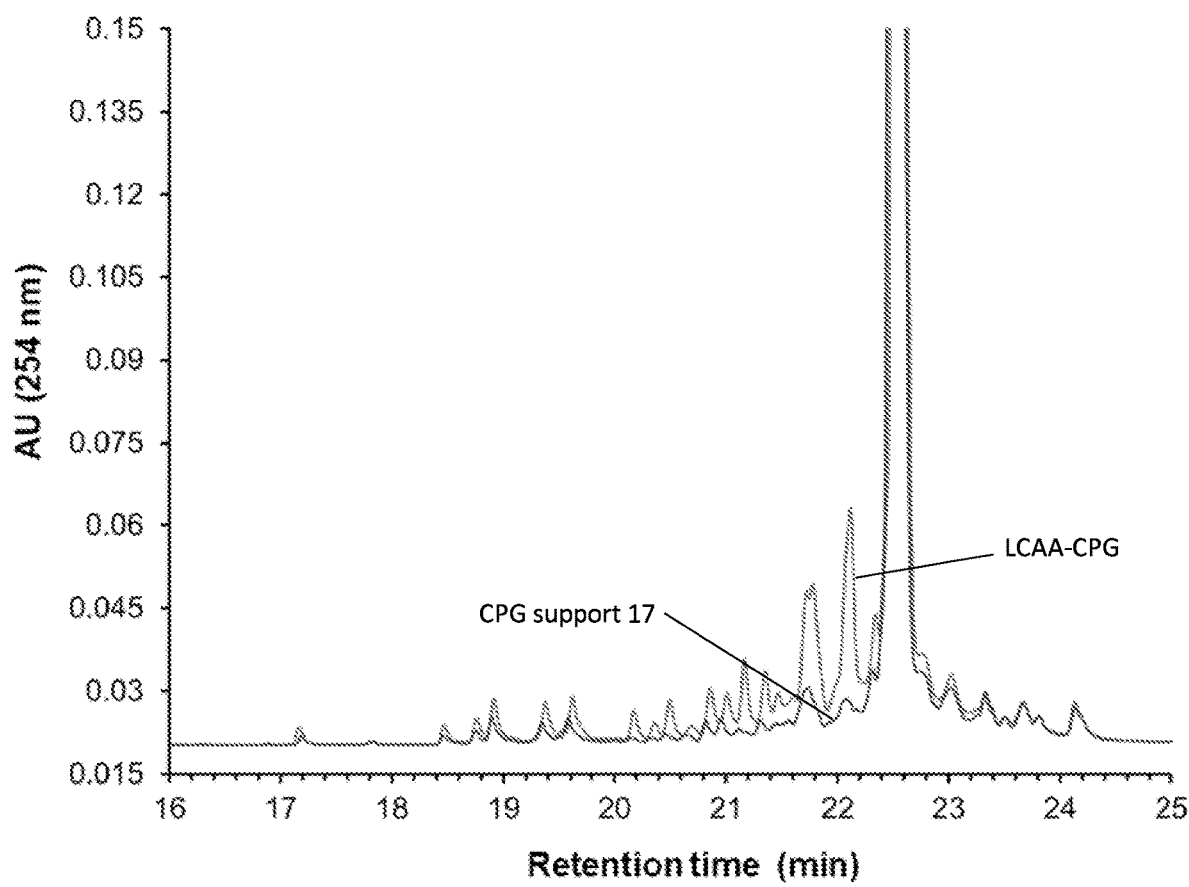
FIG. 6 is a graph of retention time versus absorbance units at 254 nm, illustrating the HPLC profiles of unpurified 5'-d(TCTTGGTTACATGAAATCCT) (SEQ ID NO: 2) produced by an embodiment of the disclosed solid support structure comprising 5 hexaethylene glycol phosphate repeating units, and comparing it to the same sequence produced using a commercial LCAA-CPG support.
Figure 7:
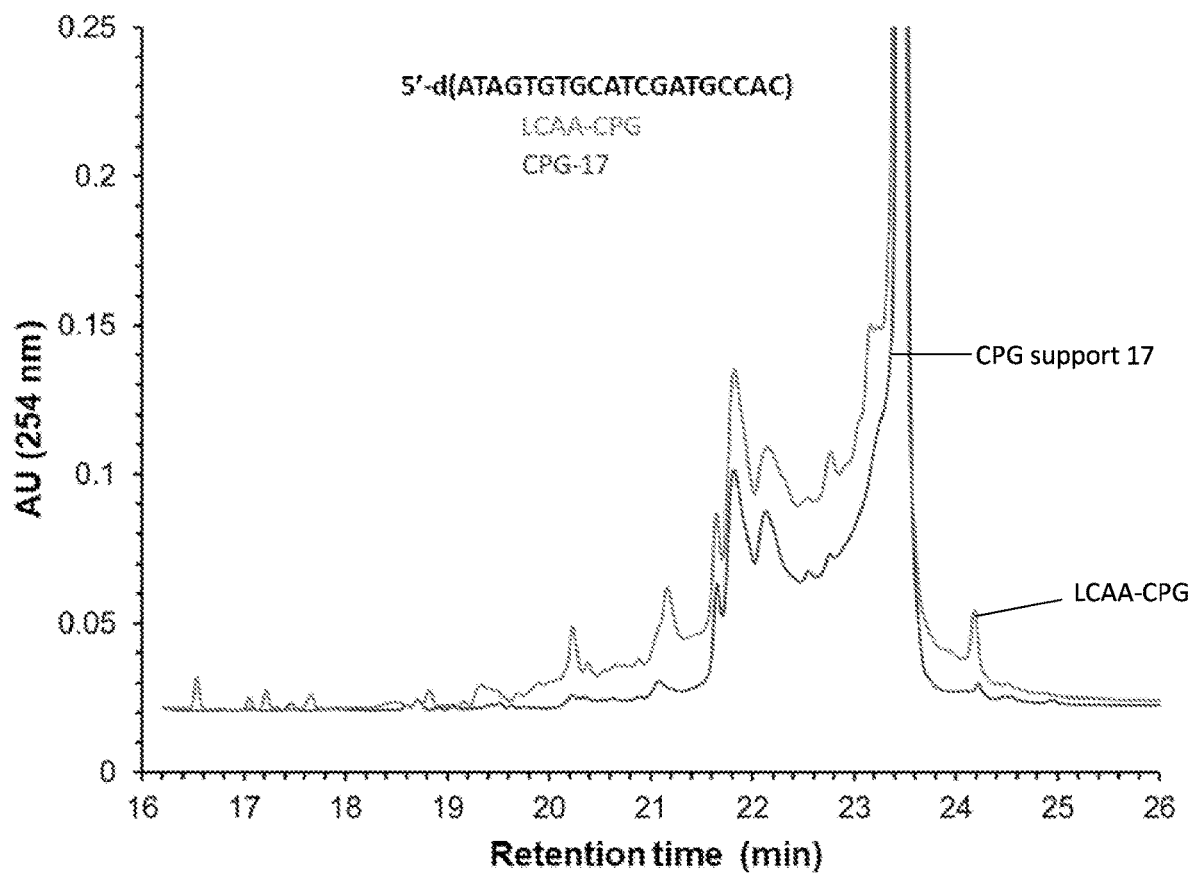
FIG. 7 is a graph of retention time versus absorbance units at 254 nm, illustrating the HPLC profiles of unpurified 5'-d(ATAGTGTGCATCGATGCCAC) (SEQ ID NO: 5) produced by an embodiment of the disclosed solid support structure comprising 5 hexaethylene glycol phosphate repeating units, and comparing it to the same sequence produced using a commercial LCAA-CPG support.
Figure 8:
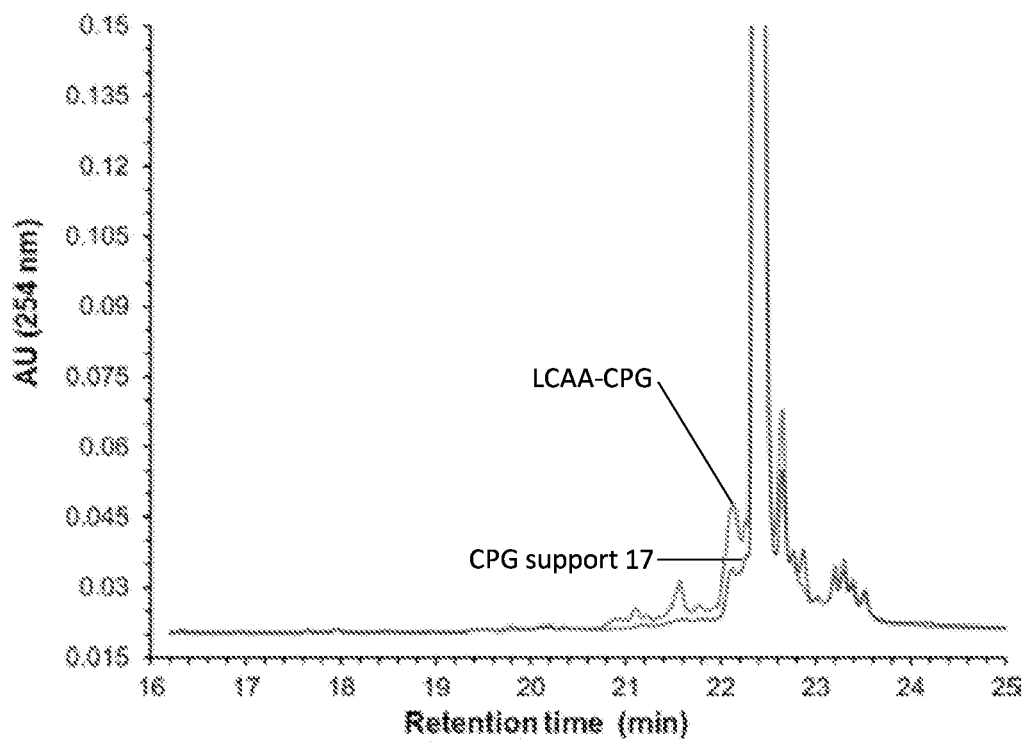
FIG. 8 is a graph of retention time versus absorbance units at 254 nm, illustrating the HPLC profiles of unpurified 5'-d(CTCTGTACCTTACGTCTTCG) (SEQ ID NO: 4) produced by an embodiment of the disclosed solid support structure comprising 5 hexaethylene glycol phosphate repeating units, and comparing it to the same sequence produced using a commercial LCAA-CPG support.
Figure 9:
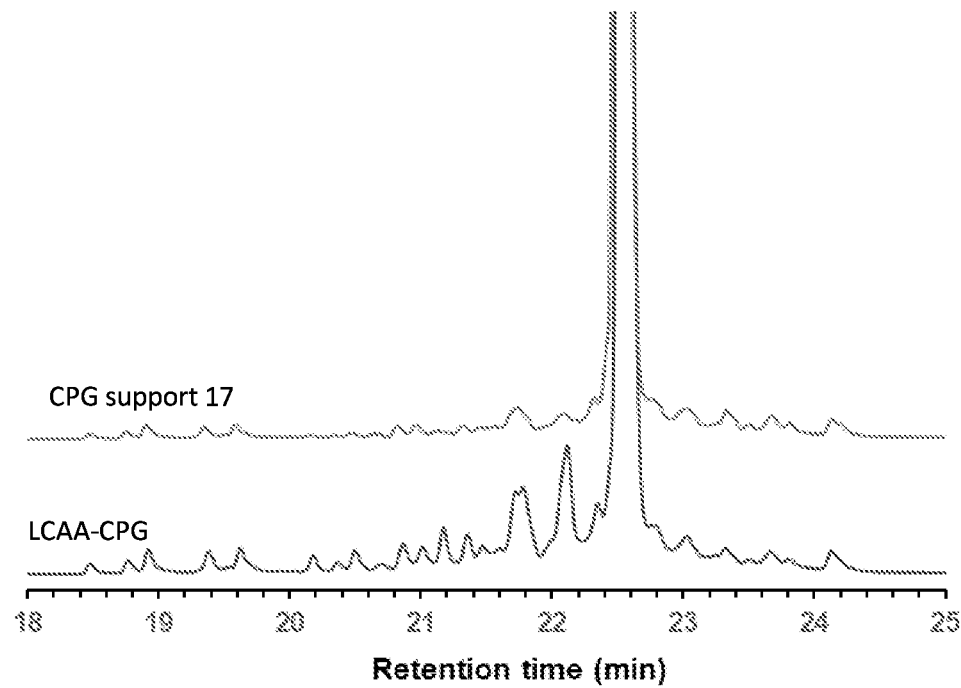
FIG. 9 provides stacked expanded HPLC profiles of the spectra from FIG. 6, illustrating the approximate 50% reduction in impurities in the product made using the CPG support, compared to the product made using the commercial LCAA-CPG support.

The solid-phase synthesis of one RNA sequence (SEQ ID. NO: 3) and three additional DNA sequences (SEQ ID NOs: 2, 4 and 5) were therefore conducted on LCAA-CPG and CPG support 14 to demonstrate that the minimization of process-related impurities was not limited to one particular nucleic acid sequence. FIG. 5 provides expanded HPLC profiles of unpurified SEQ ID NO: 3, which was released from commercial LCAA-CPG (red profile) or CPG support 17 (blue profile) after complete deprotection. FIGS. 6, 7 and 8 provide the expanded HPLC profiles for SEQ ID NOs: 2, 4 and 5, respectively, released from the disclosed CPG support 17 (blue) and LCAA-CPG (red), after complete deprotection. In each case, peak heights of each profile were normalized to the highest peak, which was then set to 0.15 absorbance unit (AU) at 254 nm. FIG. 9 provides stacked HPLC profiles for SEQ ID NO: 2 produced using a LCAA-CPG support and CPG support 17 as disclosed herein and illustrating the approximate 50% reduction in impurities in the product made using CPG support 17, compared to the product made using LCAA-CPG.

TABLE 1

Minimization of process-related impurities in synthetic nucleic acid sequences[a]

| Solid support | mPA (%)[b] | PA-pRI (%)[b] | Mi-pRI (%) |
|---|---|---|---|
| 5'-d(CTGAGTAGCGAACGTGAAGA) SEQ ID NO: 1 | | | |
| LCAA-CPG | 64 | 36 | 36 |
| CPG-14 | 77 | 23 | |
| 5'-d(TCTTGGTTACATGAAATCCT) SEQ ID NO: 2 | | | |
| LCAA-CPG | 74 | 26 | 42 |
| CPG-14 | 85 | 15 | |
| 5'-r(UCUUGGUUACAUGAAAUCCU) SEQ ID NO: 3 | | | |
| LCAA-CPG | 66 | 34 | 27 |
| CPG-14 | 75 | 25 | |
| 5'-d(CTCTGTACCTTACGTCTTCG) SEQ ID NO: 4 | | | |
| LCAA-CPG | 78 | 22 | 23 |
| CPG-14 | 83 | 17 | |
| 5'-d(ATAGTGTGCATCGATGCCAC) SEQ ID NO: 5 | | | |
| LCAA-CPG | 32 | 68 | 19 |
| CPG-14 | 45 | 55 | |

[a]mPA, main peak area; PA-pRI, peak area of process-related impurities; Mi-pRI, relative minimization of process-related impurities resulting from the use of CPG support 14 and calculated according to the following equation:
% Mi-pRI = [1 − (% PA-pRI$_{CPG-14}$ ÷ % PA-pRI$_{LCAA-CPG}$)] × 100
[b]percent of total DNA- or RNA-related peak areas.

Figure 11:
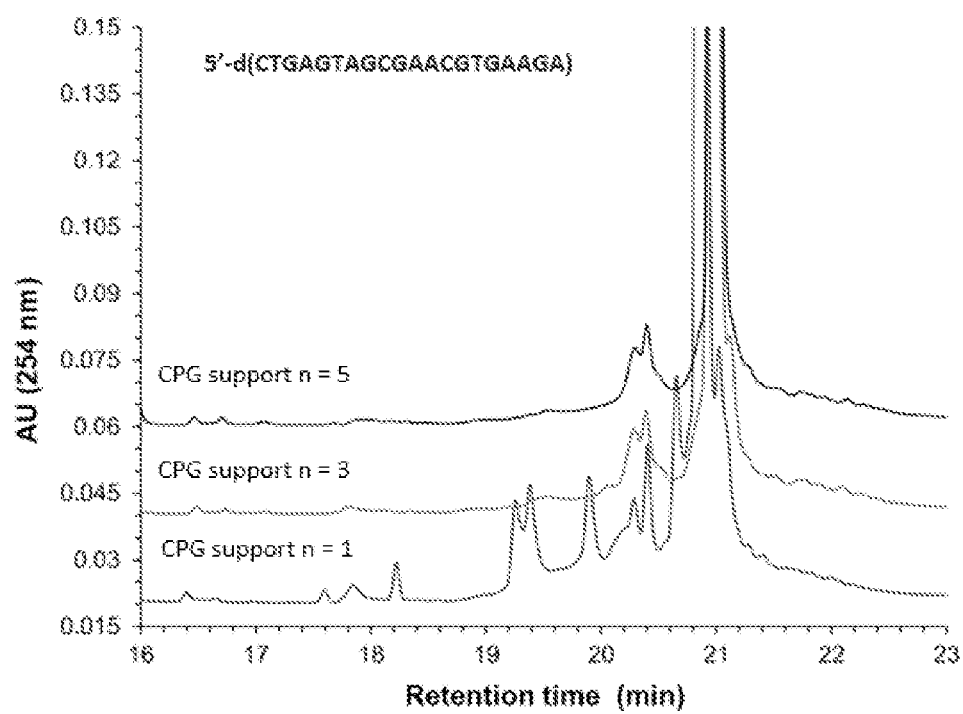
FIG. 11 provides stacked expanded HPLC profiles for sequences according to SEQ ID NO: 1 produced by CPG supports where n is 1, 3 or 5, illustrating the improved purity achieved by using supports where n is 3 and 5 compared to the purity achieved when n=1.

As shown in Table 1, synthesizing nucleic acid sequences using embodiments of the disclosed solid support structures results in significant reductions in process-related impurities. In contrast, using a similar solid support structure having only a single hexaethylene glycol spacer, i.e., n=1 in the solid phase supports from Examples 3-7, resulted in substantially less pure nucleic acid sequences than those made using solid phase supports where n was 3 or more (FIG. 11).

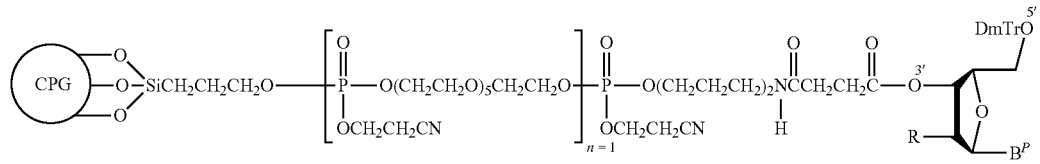

Figure 10:
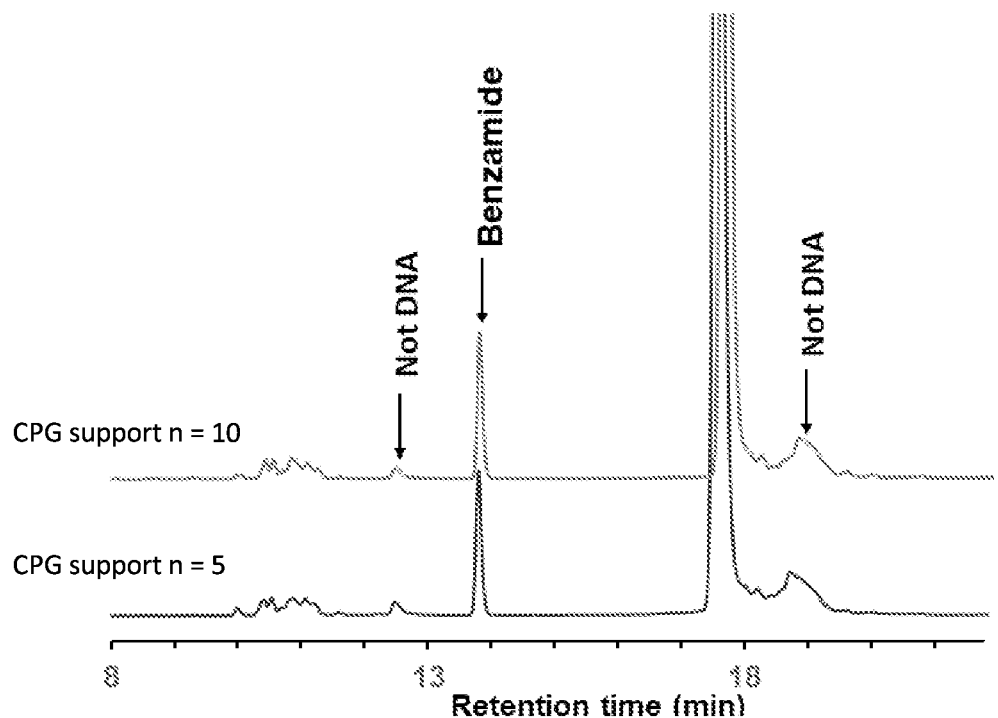
FIG. 10 provides stacked expanded HPLC profiles for sequences according to SEQ ID NO: 2 produced by CPG supports where n=5 and n=10, and illustrating that longer support structures, such as n=10, provide substantially the same purity benefits as support structures where n=5.

Table 2 provides comparative data illustrating the purity of sequences made using supports where n=1, 3, 5, 7, and 10. FIG. 10 provides a comparison of the HPLC profiles for sequences according to SEQ ID NO: 2 produced by CPG supports where n=5 and n=10. FIG. 10 demonstrates that longer support structures, such as n=10, provide substantially the same purity benefits as support structures where n=5 or 7. However, the loading on the CPG decreases as the length increases, possibly due to issues resulting from synthesizing such long chain supports. In some embodiments, the loading when n=10 is about 5-10 µmol/g, compared to about 50 µmol/g when n=5

TABLE 2

Purity of DNA sequences made using different length solid phase supports as a percentage of total peak area

| | Support | | | | |
|---|---|---|---|---|---|
| | n = 1 | n = 3 | n = 5 | n = 7 | n = 10 |
| Sequence: 5'-d(CTGAGTAGCGAACGTGAAGA) (SEQ ID NO: 1) | | | | | |
| Purity | 79% | 92% | 94% | 92% | |
| Sequence: 5'-d(TCTTGGTTACATGAAATCCT) (SEQ ID NO: 2) | | | | | |
| Purity | | | 93% | | 93% |

CONCLUSIONS

As demonstrated herein, modification of a CPG support with the addition of multiple hexaethylene glycol spacers led to the synthesis of DNA and RNA sequences of significantly greater purity that that obtained from the current, state-of-the art, LCAA-CPG support. The CPG support 14 is composed of five hexaethylene glycol spacers and was found to be as efficient as the CPG support 15, carrying seven hexaethylene glycol spacers, for minimizing process-related impurities in synthetic DNA sequences. A reduction of process-related impurities of up to 53% in synthetic nucleic acid sequences was achieved when using 14, instead of LCAA-CPG, for the solid-phase synthesis of nucleic acid sequences. Although the reduction of process-related impurities is variable and may vary depending on the composition of the nucleic acid sequence, a lower content of residual process-related impurities facilitates the removal of those impurities from the full-length nucleic acid sequences, to ultimately provide nucleic acid-based drugs of exquisite purity for safer and more efficacious therapies for human diseases.

Example 10

Typical Procedure for the Automated Preparation of a CPG Support Comprising a Universal Linker

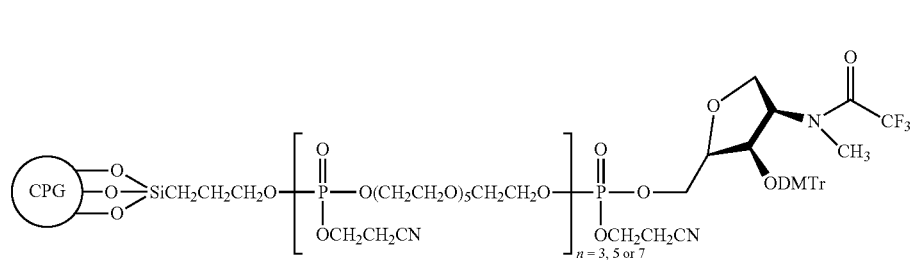

The universal support is produced using a universal linker phosphoramidite, such as the universal linker phosphoramidite shown below, according to the method illustrated in Example 4. Unreacted hydroxyl moieties are inactivated using a 1:1 (v/v) Cap A:Cap B solution as described in Example 4. And standard DNA or RNA synthesis proceeds as described in Examples 6 and 7.

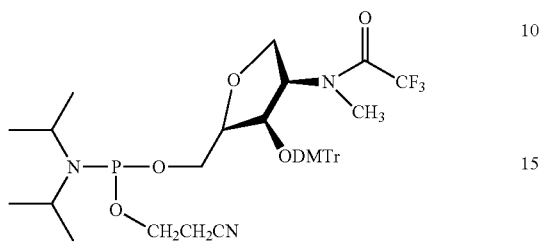

Exemplary universal linker phosphoramidite,

In view of the many possible embodiments to which the principles of the disclosed technology may be applied, it should be recognized that the illustrated embodiments are only examples of the technology and should not be taken as limiting the scope of the disclosure. Rather, the scope of the disclosure is defined by the following claims. We therefore claim as our invention all that comes within the scope and spirit of these claims.

---

We claim:

1. A solid support according to Formula I

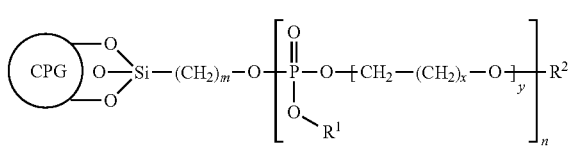

Formula I wherein:
CPG is controlled pore glass;
m is 2, 3, 4, 5 or 6;
x is 1, 2, 3, 4 or 5;
y is from 2 to 12;
n is 3, 4, 5, 6, 7, 8, 9 or 10;
$R^2$ is H,

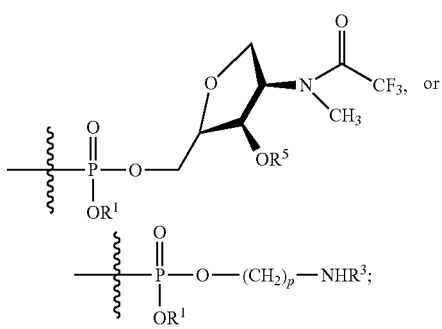

p is 2, 3, 4, 5, 6, 7, 8, 9 or 10;
$R^3$ is H or

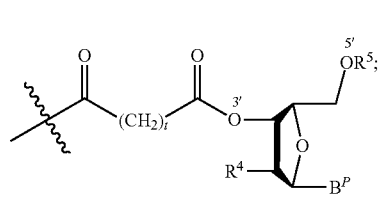

$R^4$ is H or $OR^6$;
R is PG or a nucleic acid sequence;
$R^6$ is pixyl, TBDMS, TBDPS, TMS, TES, or TIPS;
T is 1, 2, 3, or 4;
$B^P$ is a nucleic acid base where an exocyclic amine, if present, is protected;
PG is a protecting group; and
each $R^1$ independently is a thermolabile phosphate protecting group having a structure

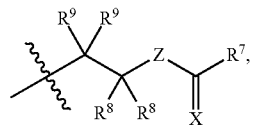

wherein:
X is O or S;
$R^7$ is H, $R^a$, $OR^a$, $SR^a$, or $N(R^b)_2$;
$R^a$ is $R^d$;
$R^b$ is H, $R^d$ or two $R^b$s together with the nitrogen to which they are attached, form a 3- to 7-membered heterocyclyl;
Z is O, S, $N(R^c)$, $C(R^c)_2$ or $C(R^c)_2C(R^c)_2$;
each $R^c$ independently is H or $R^d$, or one $R^d$ in combination with the C=X moiety and one $R^a$ or $R^b$ from $R^7$ together form a 3- to 7-membered cycloaliphatic or heterocyclyl ring;
$R^d$ is alkyl, alkenyl, alkynyl, cycloalkyl, aryl, or aralkyl;
each $R^8$ independently is H or $R^d$, or one $R^8$ together with Z forms an aryl ring;
each $R^9$ independently is H or $R^d$, or one $R^9$ and one $R^8$ together with the atoms to which they are attached, forms a moiety having a formula

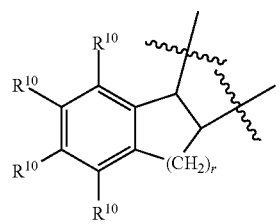

wherein r is 0 to 6; and each $R^{10}$ independently is H, $C_{1-6}$alkyl, $NO_2$, $-N(C_{1-6}alkyl)_2$, $-OC_{1-6}alkyl$, $-SC_{1-6}alkyl$, $-CN$, or halogen, provided that the aromatic ring substituted with $R^{10}$ is one carbon removed from the phosphate oxygen of Formula I.

2. The solid support of claim 1, wherein:

PG is 4,4'-dimethoxytrityl (DMTr);

m is 2, 3 or 4;

x is 1, 2 or 3;

y is from 3 to 10;

n is from 3 to 7; or a combination thereof.

3. The solid support of claim 1, wherein the solid support has a formula selected from Formula II, Formula III, Formula IV, Formula V, Formula VII, Formula XI or Formula XIII:

Formula II

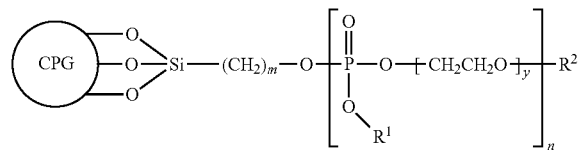

Formula III

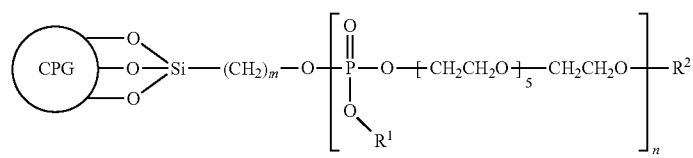

Formula IV

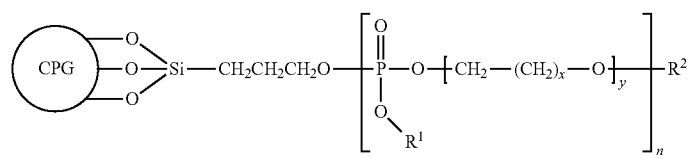

Formula V

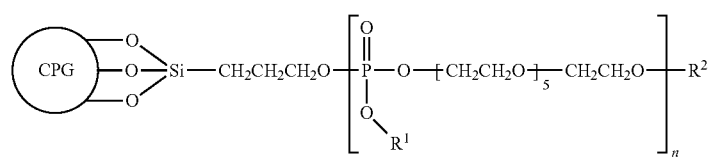

Formula VII

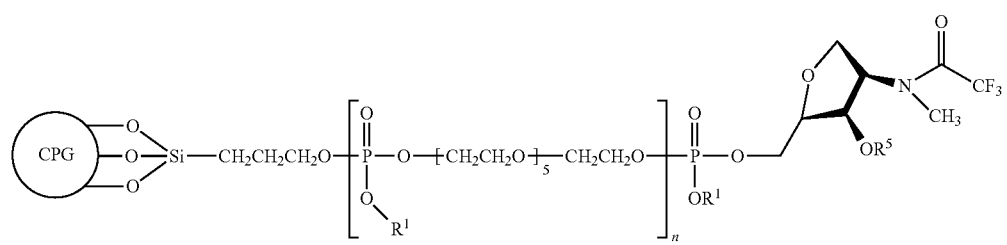

Formula XI

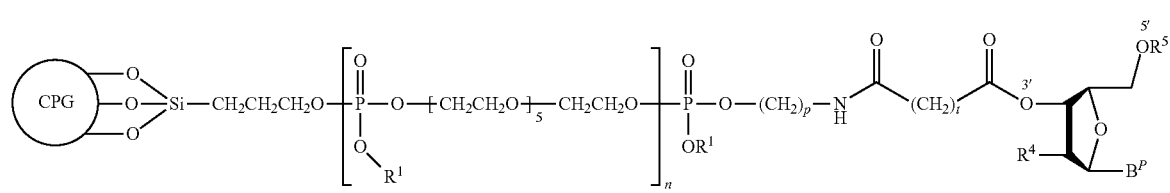

Formula XIII

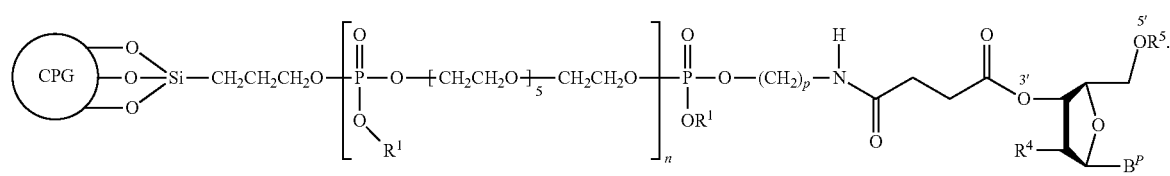

4. The solid support of claim 1, wherein n is 5.

5. The solid support of claim 1, wherein m, x, y and n are selected to produce a support backbone length from the silicon atom to the $R^2$ moiety of from 50 atoms to 400 atoms.

6. The solid support of claim 1, wherein the support backbone length is from 100 atoms to 150 atoms.

7. The solid support of claim 1, wherein $R^2$ is H.

8. The solid support of claim 1, wherein $R^2$ is

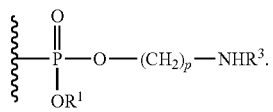

9. The solid support of claim 8, wherein p is 6.

10. The solid support of claim 8, wherein $R^3$ is H.

11. The solid support of claim 8, wherein $R^3$ is

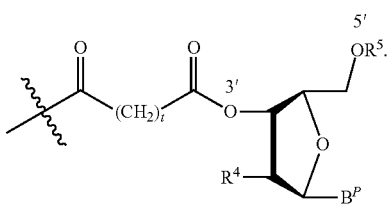

12. The solid support of claim 11, wherein $B^P$ is exocyclic amine-protected adenine, exocyclic amine-protected cytosine, exocyclic amine-protected guanine, thymine, uracil, hypoxanthine, xanthine, exocyclic amine-protected 7-methylguanine, 5,6-dihydrouracil, exocyclic amine-protected 5-methylcytosine, or exocyclic amine-protected 5-hydroxymethylcytosine.

13. The solid support of claim 11, wherein $R^4$ is H.

14. The solid support of claim 11, wherein $R^4$ is $OR^6$.

15. The solid support of claim 11, wherein:
$R^4$ is H and $B^P$ is exocyclic amine-protected adenine, exocyclic amine-protected cytosine, exocyclic amine-protected guanine, or thymine; or
$R^4$ is $OR^6$ and $B^P$ is exocyclic amine-protected adenine, exocyclic amine-protected cytosine, exocyclic amine-protected guanine, or uracil.

16. The solid support of claim 8, wherein:
$B^P$ is adenine, cytosine, or guanine, where the exocyclic amine is protected by a benzoyl (Bz), isobutyryl (iBu), phenoxyacetyl (Pac), phenylsulfonylethoxycarbonyl, p-nitrophenyloxycarbonyl, allyloxycarbonyl, or levulinyl group; or
$B^P$ is thymine or uracil.

17. The solid support of claim 1, wherein:
$R^6$ is TBDMS;
t is 2;
$R^5$ is PG: or
a combination thereof.

18. The solid support of claim 1, wherein $R^5$ is a nucleic acid sequence.

19. The solid support of claim 18, wherein:
the nucleic acid sequence comprises one or more DNA sequences; or
the nucleic acid sequence comprises one or more RNA sequences.

20. The solid support of claim 19, wherein:
the one or more DNA sequences comprise one or more antisense DNA sequences; or
the one or more RNA sequences comprise one or more antisense RNA sequences, one or more microRNA (miRNA) sequences, one or more small interfering RNA (siRNA) sequences, one or more repeat-associated small interfering RNA (rasiRNA) sequences, or combinations thereof.

21. The solid support of claim 1, wherein $B^P$ comprises a protecting group selected from benzoyl, isobutyryl, or phenoxyacetyl.

22. The solid support of claim 21, wherein $B^P$ is selected from $N^6$-benzoyl adenine ($A^{Bz}$), $N^4$-benzoyl cytosine ($C^{Bz}$), $N^2$-isobutyryl guanine ($G^{iBu}$), thymine (T), $N^6$-phenoxyacetyl adenine ($A^{Pac}$), $N^4$-phenoxyacetyl cytosine ($C^{pac}$), $N^2$-phenoxyacetyl guanine ($G^{Pac}$), or uracil (U).

23. The solid support of claim 1, wherein a loading of the support on the CPG is from 5 μmol/g to 50 μmol/g.

24. A method for synthesizing a nucleic acid sequence, comprising:
loading a solid support according to claim 1 into a DNA/RNA synthesizer; and
operating the synthesizer to produce a desired nucleic acid sequence.

25. The method of claim 24, wherein the solid support is a solid support where $R^5$ is PG; and
$R^6$ is TBDMS;
t is 2; or
$R^6$ is TBDMS and t is 2.

26. The method of claim 25, wherein $R^5$ is DMTr.

27. A kit, comprising the solid support of claim 1.

28. The kit of claim 27, further comprising a protected 2'-deoxynucleoside, ribonucleoside, and/or chemically modified nucleoside wherein an exocyclic amine on the deoxynucleoside, ribonucleoside or chemically modified nucleoside, if present, also is protected.

29. The kit of claim 28, wherein the 2'-deoxynucleoside is $DMTrdA^{Bz}$, $DMTrdC^{Bz}$, $DMTrdG^{iBu}$, or DMTrT), or the ribonucleosides is $DMTrA^{Pac}$-2'-OTBDMS, $DMTrC^{Pac}$-2'-OTBDMS, $DMTrG^{Pac}$-2'-OTBDMS, or DMTrU-2'-OTBDMS.

30. A solid support according to Formula I

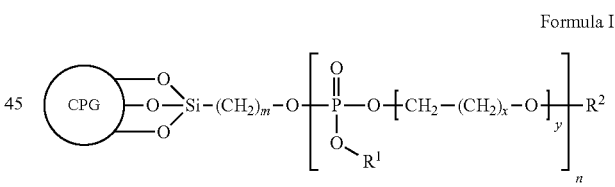

Formula I wherein:
CPG is controlled pore glass;
m is 2, 3, 4, 5 or 6;
x is 1, 2, 3, 4 or 5;
y is from 2 to 12;
n is 3, 4, 5, 6, 7, 8, 9 or 10;
$R^2$ is H,

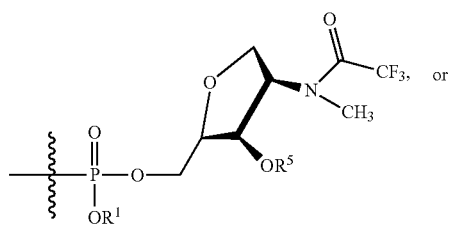

-continued

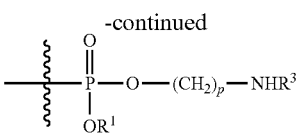

p is 2, 3, 4, 5, 6, 7, 8, 9 or 10;
R³ is H or

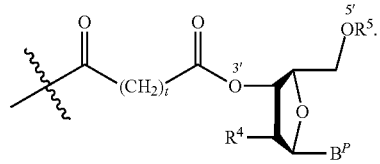

R⁴ is H or OR⁶;
R⁵ is PG or a nucleic acid sequence;
R⁶ is pixyl, TBDMS, TBDPS, TMS, TES, or TIPS;
T is 1, 2, 3, or 4;
B^P is a nucleic acid base where an exocyclic amine, if present, is protected;
PG is a protecting group; and
each R¹ independently is a thermolabile phosphate protecting group selected from:

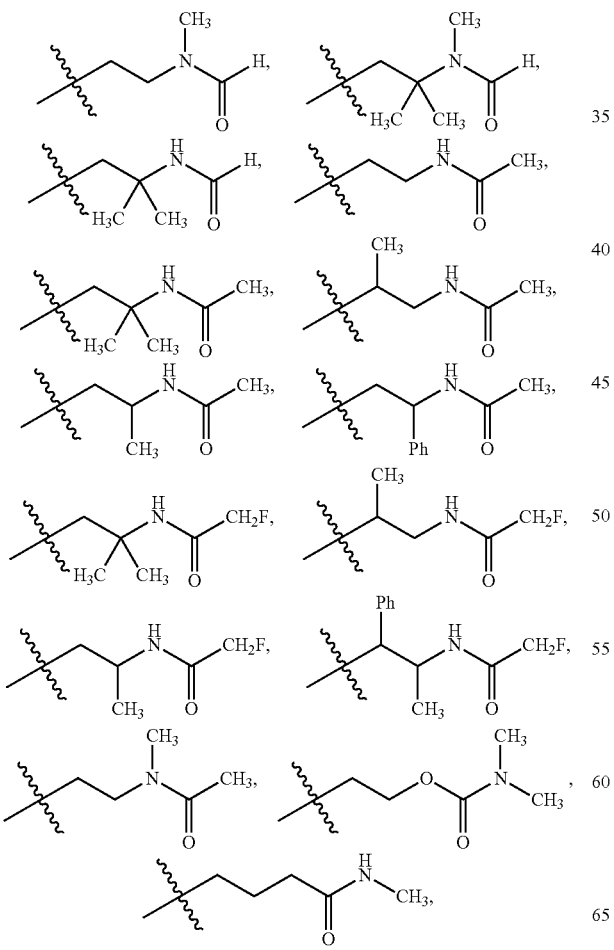

-continued

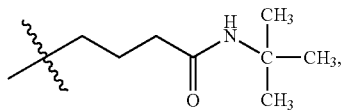

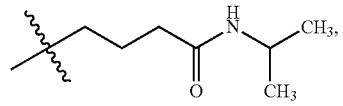

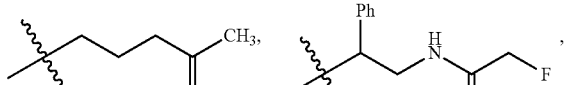

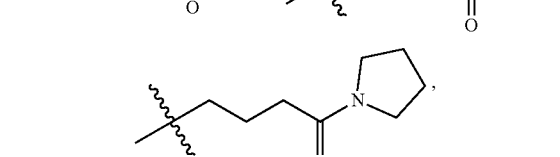

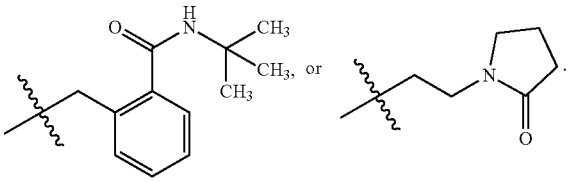

31. A solid support according to Formula I

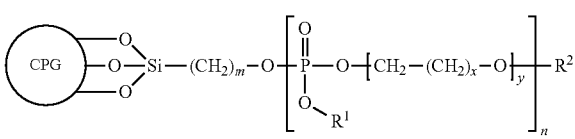

Formula I wherein:
CPG is controlled pre glass;
m is 2, 3, 4, 5 or 6;
x is 1, 2, 3, 4 or 5;
y is from 2 to 12;
n is 3, 4, 5, 6, 7, 8, 9 or 10;
each R¹ independently is $C_{1-6}$alkyl, —$(CH_2)_{1-6}$CN, —$(CH_2)_{1-6}$OR' or a thermolabile phosphate protecting group;
R' is aliphatic, aryl, or aralkyl;
R² is

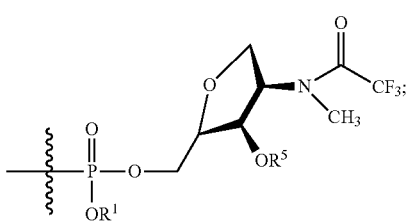

p is 2, 3, 4, 5, 6, 7, 8, 9 or 10;
R³ is H or
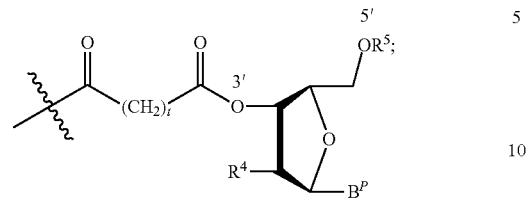
R⁴ is H or OR⁶;
R⁵ is PG or a nucleic acid sequence;
R⁶ is pixyl, TBDMS, TBDPS, TMS, TES, or TIPS;
T is 1, 2, 3, or 4;
B^P is a nucleic acid base where an exocyclic amine, if present, is protected; and
PG is a protecting group.
32. The solid support of claim 31, selected from:
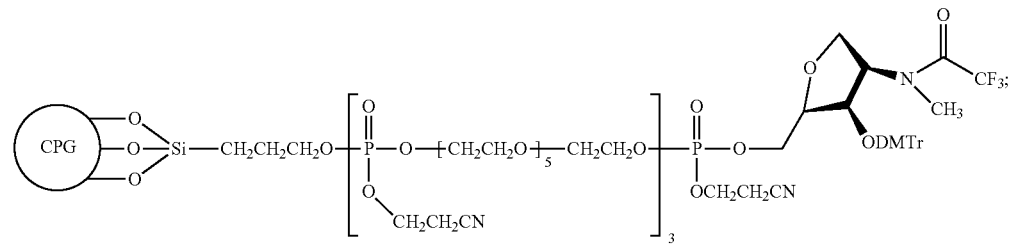
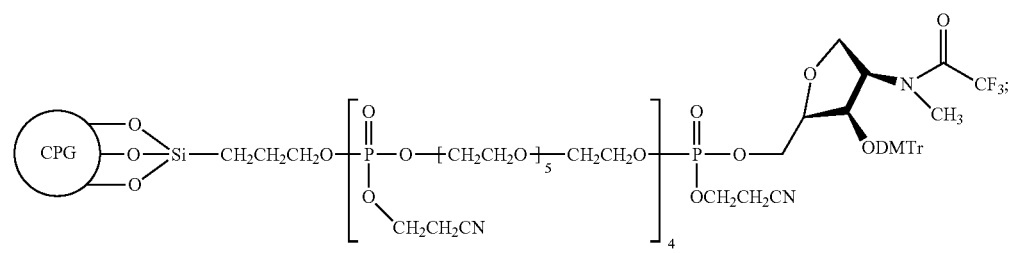
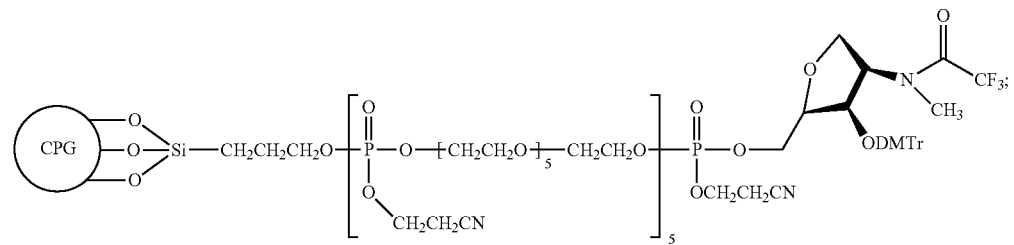
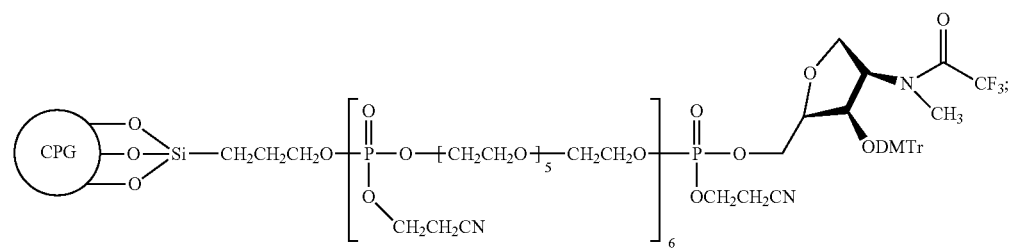

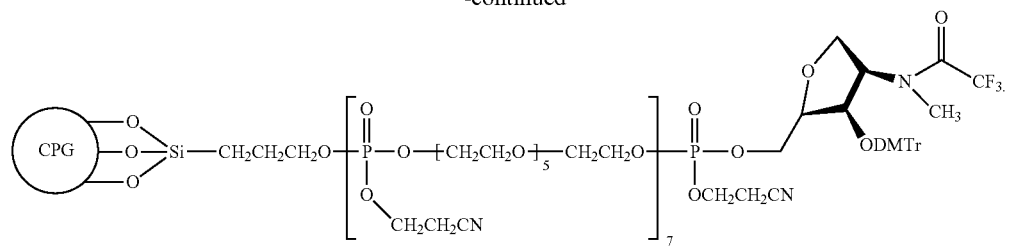
33. A kit, comprising the solid support of claim 32.
* * * * *

UNITED STATES PATENT AND TRADEMARK OFFICE
CERTIFICATE OF CORRECTION

PATENT NO. : 11,987,599 B2
APPLICATION NO. : 18/003404
DATED : May 21, 2024
INVENTOR(S) : Beaucage et al.

It is certified that error appears in the above-identified patent and that said Letters Patent is hereby corrected as shown below:

In the Claims

Column 60, Line 44. Claim 31, "controlled pre glass" should read --controlled pore glass--

Signed and Sealed this
Third Day of September, 2024

Katherine Kelly Vidal
*Director of the United States Patent and Trademark Office*